(12) United States Patent
Michot

(10) Patent No.: US 7,919,629 B2
(45) Date of Patent: Apr. 5, 2011

(54) SULPHONYL-1,2,4-TRIAZOLE SALTS

(75) Inventor: Christophe Michot, Montréal (CA)

(73) Assignees: Phostech Lithium Inc., Montreal (CA); Universite de Montreal, Montreal (CA)

( * ) Notice: Subject to any disclaimer, the term of this patent is extended or adjusted under 35 U.S.C. 154(b) by 189 days.

(21) Appl. No.: 12/097,148

(22) PCT Filed: Dec. 12, 2006

(86) PCT No.: PCT/FR2006/002712
§ 371 (c)(1),
(2), (4) Date: Dec. 18, 2008

(87) PCT Pub. No.: WO2007/068822
PCT Pub. Date: Jun. 21, 2007

(65) Prior Publication Data
US 2009/0292105 A1    Nov. 26, 2009

(30) Foreign Application Priority Data

Dec. 12, 2005  (CA) .................................... 2527575
Dec. 12, 2005  (CA) .................................... 2527802

(51) Int. Cl.
*C07D 249/12*     (2006.01)

(52) U.S. Cl. .................................. 548/263.2; 548/263.6
(58) Field of Classification Search .................. None
See application file for complete search history.

(56) References Cited

U.S. PATENT DOCUMENTS 6,680,388 B2 *  1/2004  Beier et al. ................. 548/263.8

FOREIGN PATENT DOCUMENTS

EP           0 850 932           7/1998
WO        WO 99/40025    *     8/1999

* cited by examiner

*Primary Examiner* — Rebecca L Anderson
*Assistant Examiner* — Alicia L Otton
(74) *Attorney, Agent, or Firm* — Crowell & Moring LLP

(57) ABSTRACT

The invention relates to triazole salts, to their preparation and to applications thereof. The salts have at least one anionic triazolium group which carries at least one chlorosulphonyl, fluorosulphonyl or alkoxyfluorosulphonyl group, each of the anionic groups being combined with a proton or a cation that has a valency of less than or equal to 4. The salts are useful as synthesis reagents, as chemical-reaction or polymerization catalysts, and as ion-conducting materials for electrochemical generators, supercapacitors and electrochromic devices.

22 Claims, No Drawings

SULPHONYL-1,2,4-TRIAZOLE SALTS

CROSS-REFERENCE(S) TO RELATED APPLICATION(S)

This application is a National Phase Entry of International Application No. PCT/FR2006/002712 filed on Dec. 12, 2006 designating the U.S. and claims priority under 35 U.S.C. §119 to CA 2527575 filed Dec. 12, 2005 and CA 2527802 filed Dec. 12, 2005.

The present invention relates to sulfonyl-1,2,4-triazole salts, their preparation, and uses thereof.

BACKGROUND OF THE INVENTION

Lithium bis(fluorosulfonyl) imide $(FSO_2)_2N^-Li^+$ (LiFSI), a method for the preparation thereof and use thereof in electrochemical devices are known, for instance by WO95/26056. Bis(fluorosulfonyl) imides of various onium cations are also known, for instance by WO99/40025.

Bis(fluorosulfonyl) imides have interesting properties in terms of ionic conductivity, useful for use as salt in the electrolyte of a battery, especially a lithium battery.

Bis(fluorosulfonyl)imide is prepared from bis(chlorosulfonyl)imide (HClSI), by chlorine/fluorine exchange with KF or HF. This method has many disadvantages. On the one hand, (chlorosulfonyl)imide is a product that decomposes violently in water. On the other hand, its synthesis is relatively complex. When KF is used for Cl/F exchange, the exchange strongly depends on the solvent in which the reaction takes place. Thus, tests implemented in nitromethane made by a specialist in industrial fluorine chemistry, have been abandoned, because the nitromethane causes the formation of dangerous nitrous vapors in the reactor. Attempts to find an alternative solvent have proved unsuccessful. The yield of the reaction and especially the formation of impurities such as FSO salt, probably resulting from the decomposition of (chlorosulfonyl)imide, make this kind of synthesis uninteresting at an industrial scale. When the Cl/F exchange is carried out with HF, it is necessary to operate at high temperatures (100° C. and above), and the yield of the reaction is at most about 60%, the product containing a significant amount of fluorosulfonic acid, probably resulting from the decomposition of bis(chlorosulfonyl)imide. This alternative process is also uninteresting at an industrial scale. Bis(fluorosulfonyl)imide synthesis has been abandoned by two important industrial specialists in fluorine chemistry, because furthermore, the raw product, HClSI, is difficult to access at an industrial scale.

Bis(fluorosulfonyl)imide can also be prepared by reacting fluorosulfonic acid with urea. This synthesis gives a non reproducible reaction yield (typically between 20 and 40%), it is very exothermic and the reaction medium is very corrosive. The process to separate bis(fluorosulfonyl)imide formed from the fluorosulfonic acid reagent is complex and makes the synthesis inconvenient on an industrial scale. Attempts to improve the process by carrying out the synthesis in a solvent were unsuccessful. The implementation of this synthesis method has also been abandoned by industrial specialists in fluorine chemistry.

It thus appears that the use of bis(fluorosulfonyl)imides is particularly complex to implement. Despite intensive efforts for nearly ten years in collaboration with renowned academic and industrial experts of fluorine chemistry, production on an industrial scale of bis(fluorosulfonyl)imides could not be implemented.

EP-0 850 920 describes ionic compounds in which the anion is a pentacycle, in particular of the triazole type, and the cation is a metallic cation, an organometallic cation or an onium ion.

Some of these compounds comprise a nitrile substituent on the pentacycle, for example:

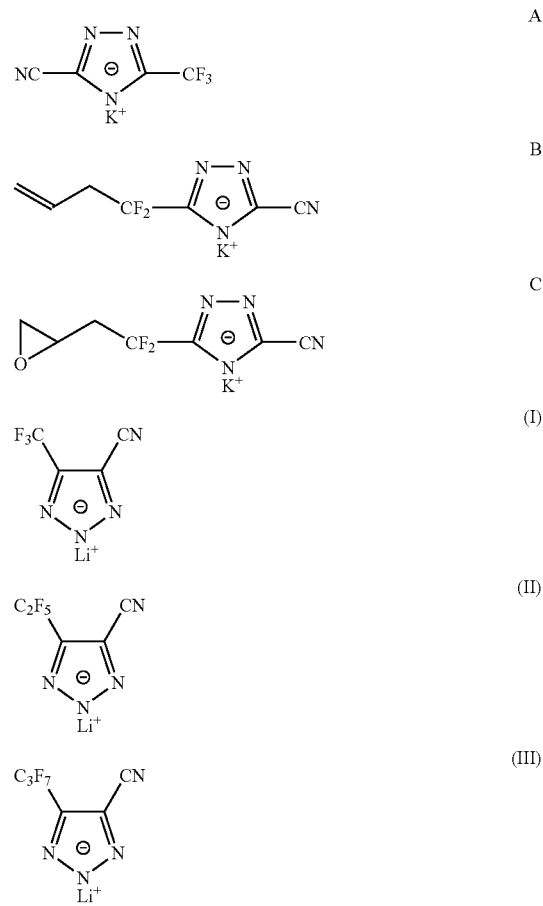

These compounds have a low thermal stability because of the possible polymerization of the —CN. It is known that nitrile derivatives can form triazine bonds by addition reaction under the effect of heat. This makes it difficult to efficiently dry the hygroscopic lithium salts and highly coloured products are rapidly obtained when drying is carried out at a temperature of about 100° C. and more. Moreover, because of the presence of the —CN group, performances of these salts, during the cycling of a battery in which they are used, are insufficient relatively to a lithium electrode in polymer technology, and even worse with a liquid or gel electrolyte. The performances are also bad in lithium-ion batteries which have a carbon anode. The limited thermal stability can also be disadvantageous when the compounds are intended for use as ionic liquid.

The compounds (A), (B) and (C) are obtained from the corresponding diazonium. However, the diazonium compounds are potentially dangerous. Particularly, the one derived from 3-trifluoromethyl-5-amino-1,2,4-triazole is a powerful explosive in dry state, despite the presence of the —CF₃ group.

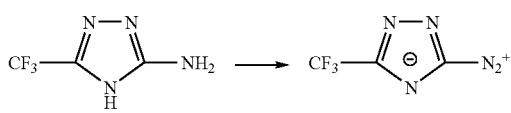

Compounds I, II and III are obtained by reaction of sodium azide with the corresponding alkynes in an organic solvent.

On the one hand, the alkynes used are uncommon and difficult to access compounds, and on the other hand, sodium azide is a dangerous compound, potentially explosive and very toxic. Hence, it is particularly difficult to develop such chemical processes at an industrial scale.

Other compounds described in EP-0 850 920 comprise a —$SO_2R_F$ in which $R_F$ is a perfluoroalkyl group, for example compounds

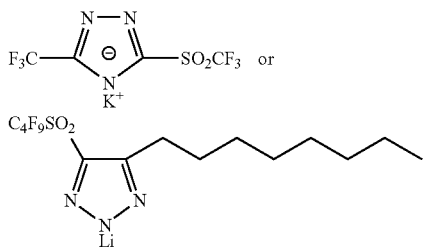

These compounds are obtained from a perfluoroalkylsulfonic reactant and either a triazole diazonium or an alkyne. On the one hand, perfluoroalkylsulfonic reactants are obtained by electrofluorination and are expensive. On the other hand, the triazole diazonium and the alkynes have the drawbacks mentioned earlier. Moreover, the synthesis of the particular compound 3-trifluoromethyl-5-trifluoromethanesulfonyl-1,2,4-triazole is carried out in an flammable organic solvent and not in water as previously, which again increases the risk on an industrial scale. Considering the synthesis and precursors, a major specialist in fluorine chemistry has abandoned exploration of the synthesis of this product.

EP-0 850 920 further describes compounds which have two perfluoroalkyl substituents, for instance the compounds

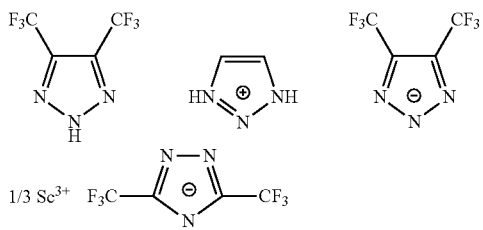

4,5-ditrifluorométhyl-1,2,3-triazole is obtained by reaction of hexafluorobutyne with $NaN_3$, which is a dangerous, potentially explosive and very toxic compound.

3,5-ditrifluoromethyl-1,2,4-triazole is obtained from trifluoroacetic acid and hydrazine by a process described in particular by Abdul-Ghani & Tipping, [J. Fluorine Chem., 72 (1995) 95], according to the following reaction scheme:

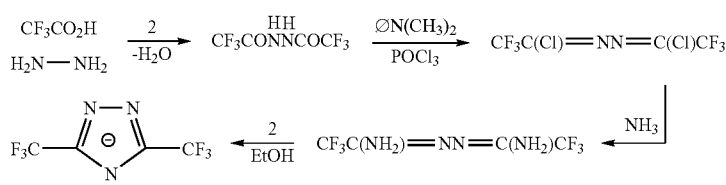

These products provide disappointing results especially in terms of electrochemical stability and of conductivity, $CF_3$ groups alone being not enough electro attractive.

SUMMARY OF THE INVENTION

The purpose of the present invention is to provide ionic compounds which do not have the drawbacks of the above-mentioned prior art compounds, namely, which are easier to prepare, from less dangerous reactants, which have good conductivity, thermal stability and electrochemical stability properties, and which can be used at industrial scale. Important research works have allowed inventors to determine anions derived from 1,2,4-triazole and which do not have any N≡C or substituent, in order to improve the performances, the costs and the industrialization opportunities. These products can be obtained from industrial precursors of the organic chemistry such as dithiosemicarbazide, dithiobiurea $H_2NC(=S)NHNHC(=S)NH$, trifluoromethanecarboxylic acid or trifluoroethanol $CF_3CH_2OH$.

Accordingly, the present invention is related to chlorosulfonyl ionic compounds, to their use for the preparation of fluorinated ionic compounds, and to various uses of the fluorinated ionic compounds A chlorosulfonyl ionic compound according to the present invention comprises at least one anionic part associated with at least one cationic part M in a sufficient number to grant electronic neutrality to the whole compound, wherein M is $H^+$, or a cation of valence m ($1 \leq m \leq 4$), and wherein the anionic part has the formula

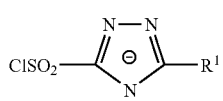

(I)

wherein $R^1$ represents a $ClSO_2$— group;

a group $R_F$ selected from $HCF_2$—, $HCF_2CF_2$—, and linear or branched perfluoroalkyl groups having 1 to 12 carbon atoms wherein the chain may optionally be interrupted by at least one divalent oxygen atom linked to two carbon atoms;

a group of formula

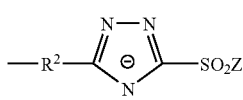
(Ia)

wherein Z is Cl and $R_2$ is a linear or branched perfluoroalkylene group having 2 to 12 carbon atoms wherein the chain may optionally be interrupted by at least on divalent oxygen atom linked to two carbon atoms.

In the following text, TrM represents an 1,2,4-triazole group, M represents H or a cationic group, and $Tr^-$ represents the anionic group. A compound I can then be written $ClSO_2$-TrM-$R^1$.

The compounds $ClSO_2$-TrM-$SO_2Cl$ (MBCST), $ClSO_2$-TrM-$CF_3$ (MTCST) and $ClSO_2$-TrM-$R^2$-TrM-$SO_2Cl$ may be particularly cited as compounds I.

Examples of $R_F$ groups are $HCF_2$—, $HCF_2$—$CF_2$—, $CF_3$—$CF_2$—$CF_2$—O—$CF(CF_3)$—, $CF_3$—$CF_2$—$CF_2$—O—$CF(CF_3)$—$CF_2$—$CF(CF_3)$—, $C_2F_5$—, $C_4F_9$— groups.

When M is a cationic group of valence m, it may be chosen among oxonium, nitrosonium, and ammonium cations, metal cations of valence m, organic cations of valence m and organometal cations of valence m. Hydroxonium, oxonium, ammonium, amidinium, guanidinium, pyridinium, quinolinium, imidazolium, pyrazolium, imidazolinium, triazolium, sulfonium, phosphonium, phospholium, phosphorolium, iodonium, carbonium, pyridazinium, pyrimidinium, pyrrolidinium, thiazolium, oxazolium, uronium, thiouronium, pyrazinium, piperazinium, piperidinium, pyrrolium, pyrizinium, thiomorpholinium and morpholinium cations may be mentioned as examples of organic cations.

Compounds I wherein M is H, $NH_4$ or an alkali metal cation are of particular interest for the preparation of the corresponding fluorinated ionic compounds.

Generally, a compound I having one or two $ClSO_2$— groups can be obtained from the corresponding thiol compound having one or two —SH groups, by oxydative chlorination of the thiol in water.

3,5-dimercapto-1,2,4-triazole is a dithiol particularly useful for the preparation of symmetric compounds I. It can be obtained from 2,5-dithiobiuree by cyclisation in presence of a base such as LiOH, NaOH or triethylamine (according to the process described in GB-1049053), according to the reaction scheme:

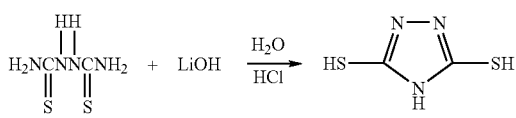

The MBCST compound can be obtained by oxydative chlorination from 3,5-dimercapto-1,2,4-triazole in water ($Cl_2$/$H_2O$), in presence of NaCl, according to the following reaction diagram:

(MBFST)

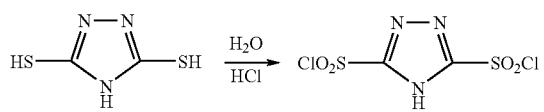

A HS-TrH-$R^1$ compound in which $R^1$ is of the type $R_F$ can be obtained by reacting the fluoride acid $R^1COF$ or the chloride acid $R^1COCl$ with the thiosemicarbazide $H_2NC(=S)NHNH_2$ in the presence of a base, followed by cyclization in the presence of a base (according to the process described in U.S. Pat. No. 4,226,873 and in Vershilov, S. V., Popova, L. M., Mungalov, V. E., and Ryabinin, N. A., Zh. Prikl. Khim., 1994, vol. 67, No7, p. 1124), according to the following reaction scheme:

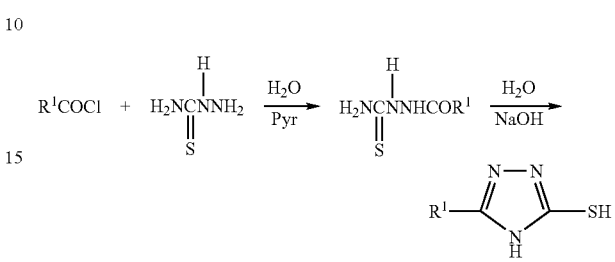

A dianionic compound can be obtained in the same manner by reacting a compound $R^2(COF)_2$ or $R^2(COCl)_2$ with the thiosemicarbazide $H_2NC(=S)NHNH_2$ in the presence of a base, followed by cyclization in the presence of a base, according to the following reaction scheme:

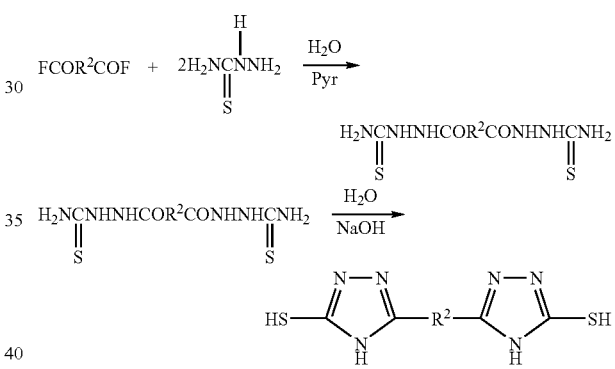

The HTCST compound can be obtained by oxidative chloration of the corresponding thiol (a product sold in particular by Toronto Research Chemicals Inc.), according to the following reaction scheme:

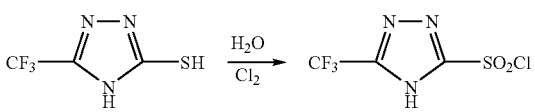

Similarly, a compound I in which R is —$(CF_2)_2$-TrM-$SO_2Cl$, can be obtained by oxidative chlorination of the following thiol

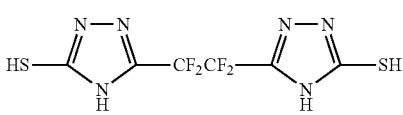

Generally, a compound I of formula Cl—$SO_2$-TrH—$(CF_2)_z$-TrH-$SO_2Cl$ (preferably $1 \leq z \leq 6$) can be obtained by oxidative chlorination of the corresponding thiol HS-TrH—$(CF_2)_z$-TrH—SH.

A thiol HS-TrH—(CF$_2$)$_z$-TrH—SH can be obtained by reacting the thiosemicarbazide with a ClC(=O)—(CF$_2$)$_z$—C(=O)Cl compound, which is sold in particular by SynQuest Labs, particularly for z=2, 3 and 4).

In the various processes for preparing compounds I, a thiol or a dithiol in which the cation associated with the anionic triazole group is the proton is preferably used, and a compound I in which M is H is obtained. The corresponding compounds I comprising a different cation can be obtained by conventional cation exchange reaction.

A compound I is a precursor for the preparation of a fluorosulfonyl ionic compound II, which constitutes another object of the present invention. A fluorosulfonyl compound comprises at least one anionic part associated with at least one cationic M' part in a sufficient number to ensure the electronic neutrality of the whole, and it is characterized in that M' is H$^+$, or a cation having the valency m ($1 \leq m \leq 4$), and in that the anionic part is of the formula

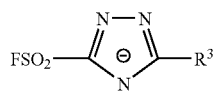
(II)

wherein R$^3$ represents:
- a FSO$_2$— group;
- a group R$_F$ selected from HCF$_2$—, HCF$_2$CF$_2$—, and linear or branched perfluoroalkyl groups having 1 to 12 carbon atoms wherein the chain may optionally be interrupted by at least one divalent oxygen atom linked to two carbon atoms;
- a group of formula

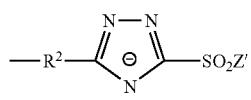
(IIa)

wherein Z' is F and R$_2$ is a linear or branched perfluoroalkylene group having 2 to 12 carbon atoms wherein the chain may optionally be interrupted by at least one divalent oxygen atom linked to two carbon atoms.

Compounds FSO$_2$-TrM'-SO$_2$F (M'BFST), FSO$_2$-TrM'-CF$_3$ (M'TFSTF) and FSO$_2$-TrM'-R$^2$-TrM'-SO$_2$, wherein TrM' represents an anionic group 1,2,4-triazole associated with cation M', are specific examples of compounds II.

When M' is a cationic group of valency m, it may be selected from oxonium, nitrosonium, and ammonium cations, metal cations having the valency m, organic cations having the valency m and organometal cations having the valency m. Hydroxonium, oxonium, ammonium, amidinium, guanidinium, pyridinium, quinolinium, imidazolium, pyrazolium, imidazolinium, triazolium, sulfonium, phosphonium, phospholium, phosphorolium, iodonium, carbonium, pyridazinium, pyrimidinium, pyrrolidinium, thiazolium, oxazolium, uronium, thiouronium, pyrazinium, piperazinium, piperidinium, pyrrolium, pyrizinium, thiomorpholinium and morpholinium cations may be mentioned as examples of organic cations.

Generally, a fluorosulfonyl compound II can be obtained from the corresponding chlorosulfonyl compound I by a Cl/F exchange reaction. The process consists in reacting a compound I with a fluoride precursor capable to replace the chlorine atom of the SO$_2$Cl group(s) of compound I with a fluorin atom.

In a first embodiment, cholorosulfonyl I is reacted with an alkaline metal fluoride, e.g. KF. This reaction can be carried out in an organic solvent (e.g. MeNO$_2$, DMSO, CH$_3$CN, dioxane, sulfolane, glymes . . . ), in a water/organic solvent mixture (e.g. in a water/dioxane mixture), or in water.

In a second embodiment, compound I is reacted with ZnF$_2$ in pyridine.

In a third embodiment, compound I is reacted with a fluorhydric acid onium, for example with the HF-pyridine C$_5$H$_5$N.(HF)$_x$ complex.

In a fourth embodiment, compound I is reacted with anhydrous HF. The advantage of this embodiment is that it does not generate unwanted by-products such as KCl. It is particularly advantageous at industrial scale. The implementation of this process in the presence of LiF or of LiCl yields the anhydrous lithium salt.

Conventional ion exchange reactions are implemented to modify the cation of compound II if required. They are carried out for example with a halide, an acetate or a sulfamate of an organic cation M' intended to replace the initial cation M, or with a halide, a nitrate, a carbonate or a carboxylate of a metallic cation M' intended to replace the initial cation M, or with HF.

Some examples are given below, the generalisation thereof is in the scope of the person with normal skills.

Compound KBFST, represented by the formula F—SO$_2$-TrK—SO$_2$F, can be obtained from the corresponding chlorinated BBCST compound via exchange with KF in a mixture of water/dioxane, according to the following reaction scheme:

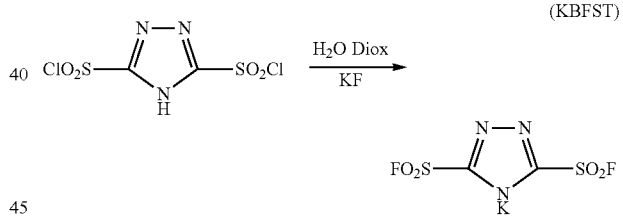
(KBFST)

The HBFST compound in acid form is obtained from the HBCST compound by exchanging Cl/F using HF.

A LiBFST compound in the form of lithium salt can be obtained by an exchange between LiNO$_3$ and the compound KBFST in acetonitrile ACN, elimination of insoluble KNO and recovery of the LiBFST compound.

A LiBFST compound in the form of lithium salt can also be obtained by reaction of HBCST with LiF in HF, according to the following reaction scheme:

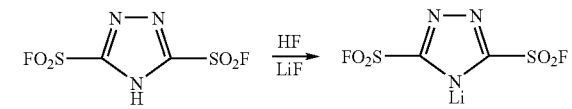

A LiBFST compound in the form of lithium salt can also be obtained by reaction of HBFST with Li$_2$CO$_3$ in water, or by reaction of the HBFST compound with the lithium disalt of oxalic acid in acetonitrile. MBFST compounds in which M is another cation (for example Na, K or Ag) can be obtained from the appropriated carbonate.

A compound II in which M' is an alkali metal cation, particularly $H^+$, $Li^+$, $Na^+$ or $K^+$, more particularly $Na^+$ or $K^+$, or a metallic $Ag^+$ cation, can be used for the preparation of a compound II in which the cation M' is different, by a metathesis reaction. For example, reaction in water of NaCl with a compound II-Ag makes it possible to prepare a solution of the compound II-Na, the equilibrium being modified by precipitation of AgCl. The reaction in water of a compound II-Li with KF allows preparation of the compound II-K, LiF being more insoluble than KF. The reaction in THF of a compound II-K with LiCl, relatively soluble in this solvent, allows preparation of the compound II-Li, with the precipitation of KCl which is formed. The reaction of a compound II-K with the complex $(ScCl_3)(THF)_3$ allows preparation of a compound II-Sc, for example $Sc(BFST)_3$ starting from KBFST. Such a process can be implemented in many solvents, particularly in ionic liquids, by reacting $LiBF_4$, $LiClO_4$ or $LiNO_3$ with a compound II-K of the invention, to form the corresponding compound II-Li induced by precipitation of insoluble $KBF_4$, $KClO_4$ or $KNO_3$.

The metathesis reaction also allows preparation of II-onium compounds, especially by the reaction of a compound II-K with a chloride, an acetate or a sulfamate of the onium ion that can be obtained by conventional synthesis processes. The metathesis reaction can also be implemented from tetrafluoroborates, from perchlorates, and from nitrates, many of which being commercially available. The replacement of the $K^+$ cation by an onium cation makes the compound II-M' insoluble, especially in water. Mention may be made for example of the preparation in water of 2,2'-azobis[2-(2-imidazolinium-2-yl)propane 3-trifluoromethyl-5-fluorosulfonyl-1,2,4-triazole which is slightly soluble in water and which has the formula

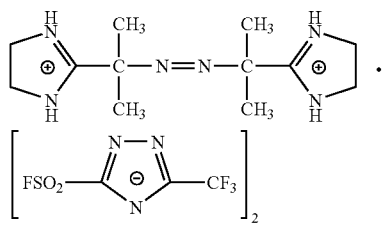

starting from 2,2'-azobis[2-(2-imidazoline-2-yl)propane]hydrochloride and two equivalents of the potassium salt of 3-trifluoromethyl-5-fluorosulfonyl-1,2,4-triazole (KTFST), both soluble in water.

The same compound II-onium can also be obtained by reacting the hydrochloride with two equivalents of the potassium salt KTFST in an organic solvent such as acetonitrile, and then by eliminating the precipitate of KCl thus formed, by filtration or centrifugation.

By a similar process, a compound II-M' in which M' is a diphenyl iodonium cation can be prepared by reacting a chloride with a II-K compound, in solution in propylene carbonate.

In all cases, the II-M' compound obtained can either be isolated for its future use, or used in the form of the solution in which it is obtained.

A compound I or a compound II is a precursor for the preparation of a fluoroalkoxysulfonyl ionic compound III which is a further object of the present invention. A fluoroalkoxysulfonyl compound III comprises at least one anionic part associated with at least one cationic part M" in a sufficient number to ensure electronic neutrality to the whole compound, wherein M" is $H^+$, or a cation having the valence m ($1 \leq m \leq 4$), and wherein the anionic part has one of the formulae

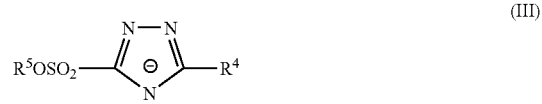 (III)

or $R_F\text{-TrM-}SO_2\text{—O—}R^9\text{—O—}SO_2\text{-TrM-}R_F$ (III')

wherein $R^4$ represents:
  un groupement $R^5\text{—O—}SO_2\text{—}$;
  a group $R_F$ selected from $HCF_2\text{—}$, $HCF_2CF_2\text{—}$, and linear or branched perfluoroalkyl groups having 1 to 12 carbon atoms wherein the chain may optionally be interrupted by at least one divalent oxygen atom linked to two carbon atoms;
  a group of formula

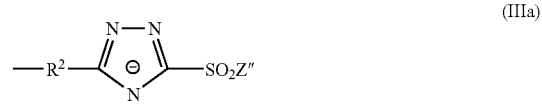 (IIIa)

wherein Z" is $R^5\text{—O—}$ and $R^2$ is a linear or branched perfluoroalkylene group having 2 to 12 carbon atoms wherein the chain may optionally be interrupted by at least one divalent oxygen atom linked to two carbon atoms;
  $R^5$ represents a $R^6CH_2\text{—}$ group, a $R^6R^7CH\text{—}$ group or a $R^6R^7R^8CH\text{—}$ group, and $R^9$ represents a $\text{—}R^6CH\text{—}$ or a $\text{—}R^6R^7C\text{—}$ fluoroalkylene group, wherein $R^6$, $R^7$ and $R^8$ groups represent a perfluorinated linear or branched alkyl group preferably having 1 to 12 carbon atoms, the chain of which is optionally interrupted by at least one divalent oxygen atom linked to two carbon atoms.

$R^5$ may be for instance a group selected from $CF_3\text{—}CH_2\text{—}$, $C_2F_5\text{—}CH_2\text{—}$, $C_4F_9\text{—}CH_2\text{—}$ and $CH(CF_3)_2\text{—}$.

As specific examples of compounds III, mention may be made of $R^5\text{—O—}SO_2\text{-TrM"-}SO_2\text{—O—}R^5$, $R^5\text{—O—}SO_2\text{-TrM"-}R^2\text{-TrM"-}SO_2\text{—O—}R^5$ and $R^5\text{—O—}SO_2\text{-TrM"-}CF_3$, wherein TrM" represents an anionic 1,2,4-triazole group associated to cation M".

When M" is a cationic group of valence m, it may be selected from hydroxonium, oxonium, nitrosonium, ammonium cations, metal cations of valence m, organic cations of valence m and organometal cations of valence m. As an organic cation, mention may for example be made of hydroxonium, oxonium, ammonium, amidinium, guanidinium, pyridinium, quinolinium, imidazolium, pyrazolium, imidazolinium, triazolium, sulfonium, phosphonium, phospholium, phosphorolium, iodonium, carbonium, pyridazinium, pyrimidinium, pyrrolidinium, thiazolium, oxazolium, uronium, thiouronium, pyrazinium, piperazinium, piperidinium, pyrrolium, pyrizinium, thiomorpholinium and morpholinium.

Generally, a fluoroalcoxysulfonyl III compound may be obtained by reacting an alcohol $R^5\text{—OH}$ or a diol $HO\text{—}R^8\text{—}OH$ or the corresponding alcoolate with the corresponding chlorosulfonyl I compound or the corresponding fluorosulfonyl II compound, preferably with the compound I. The compound III thus obtained can then be transformed by ion exchange or metathesis reactions, by methods similar to those described above for compounds II.

In a first embodiment, a compound $ClSO_2$-TrM-$R^1$ having one or two $SO_2C_1$ or $SO_2F$ groups is reacted with an alcoolate, for example a sodium alcoolate $R^5$—O—Na in THF. Two examples of reaction schemes are given below, for a HBCST compound and for a HTCST compound, $R^5$ being $CF_3$.

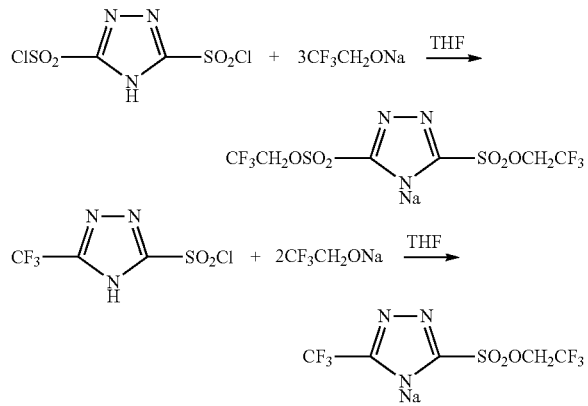

In another embodiment, a compound having a single $FSO_2$ or $ClSO_2$ group, for example the compound HTCST, is reacted with a diol HO—$R^9$—OH, according to the following reaction scheme given as an example:

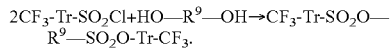

A compound I having two $ClSO_2$ groups or a compound II having either two $FSO_2$ groups or one $FSO_2$ group and one $ClSO_2$ group are precursors for the preparation of a polyionic compound IV which is another object of the present invention. A compound IV is a polymer consisting of repeat units having one of formulae

[—O$_2$S-TrM*-SO$_2$OCH$_2$—R$^9$—CH$_2$O—] or [—O$_2$S-TrM*-R$^2$-TrM*-SO$_2$OCH$_2$—R$^9$—CH$_2$O—]

wherein $R^2$ has the previously mentioned meaning, M* is $H^+$, or a cation of valence m ($1 \leq m \leq 4$), TrM* has the meaning mentioned for TrM, and $R^9$ is a linear or branched perfluoroalkylene group having preferably 2 to 12 carbon atoms wherein the chain may be optionally interrupted by at least one divalent oxygen atom linked to two carbon atoms.

When M* is a cationic group of valence m, it may be selected from nitrosonium, ammonium cations, metal cations having the valence m, organic cations having the valence m, and organometal cations having the valence m.

As an organic cation M*, mention may in particular be made of hydroxyonium, oxonium, ammonium, amidinium, guanidinium, pyridinium, quinolinium, imidazolium, pyrazolium, imidazolinium, triazolium, sulfonium, phosphonium, phospholium, phosphorolium, iodonium, carbonium, pyridazinium, pyrimidinium, pyrrolidinium, thiazolium, oxazolium, uronium, thiouronium, pyrazinium, piperazinium, piperidinium, pyrrolium, pyridinium, thiomorpholinium and morpholinium.

A compound IV is obtained by reacting a compound I or II which carries two —$SO_2Cl$ or —$SO_2F$ groups, preferably two —$SO_2Cl$ groups, with a difunctional fluoroalcohol OH—$R^9$—OH.

The following reaction scheme is given as an example, R being a —$(CF_2)_3$— group:

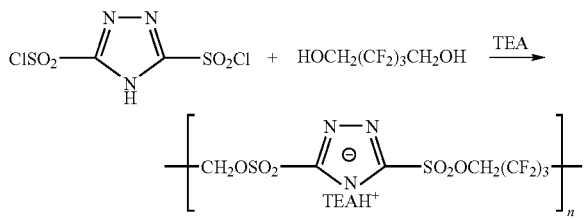

Use of reactants including the $CF_3SO_2$— group can be avoided by the presence of electroattractive groups such as $CF_3CH_2OSO_2$—, the cost of on an industrial scale being typically of about $1/10^{th}$ of that of the $CF_3SO_3H$ acid.

Also for the compounds IV, ion exchange reactions and metathesis reactions provides compounds of various cations, from compounds wherein the cation is a H or an alkaline metal cation.

The compounds II, III and IV of the present invention provide a good trade-off between performances, cost and ease of production on an industrial scale, as a result of a extensive Research and Development effort, from a great variety of products. The 3,5-difluorosulfonyl-1,2,4-triazole lithium is certainly less conductive than LiFSI, the industrialization of which could not be made, but it is as conductive as LiTFSI [LiN(SO$_2$CF$_3$)$_2$] at a lower cost, and it causes less corrosion on a collector aluminium than LiTFSI. 3-trifluoromethyl-5-fluorosulfonyl 1,2,4-triazole (CF$_3$-TrM-SO$_2$F) is more heat stable and more conductor than the counterpart 3-trifluoromethyl-5-cyano-1,2,4-triazole (CF$_3$-TrM-CN). That is why compounds of the invention are limited to those who have at least one SO$_2$F group and at least one fluoroalkyl or fluoroalkylene group. Their synthesis from the corresponding thiols can be done without major difficulty, for example by implementing an oxidative chlorination in water that changes a —SH group into a —SOCl group (whereas ClSO$_2$NLiSO$_2$Cl decomposes violently in water) and an Cl/F exchange. A compound having a SO$_2$Cl group is easily obtained from the corresponding compound having a —SH group and it presents another advantage in that the group SO$_2$Cl being carried by a heterocycle, the compound is much more stable than ClSO$_2$NLiSO$_2$Cl and therefore less sensitive to the synthesis conditions. Unlike the coordinating anions such as BF$_4$— or PF$_6$—, the fluorosulfonated anions of the present invention do not release hydrofluoric acid in the presence of water. It is known that the generation of HF induces many problems, for example in Li-Ion batteries in which the release of HF can lead to a partial dissolution of cathodes in LiMn$_2$O$_4$ or LiFePO$_4$, together with a degradation of the electrolyte. It is also known that in certain catalysis processes such as the Aza-Diels-Alder catalysis in an ionic liquid medium, the F$^-$ anion destroys the Danishefsky diene which is an intermediate compound of the reaction.

In compounds I, II, III or IV of the present invention, the cation can be H$^+$, an oxonium, a hydroxonium, a nitrosonium, an ammonium, a metallic cation with the valency m, an organic cation with the valency m or an organic metal cation with the valency m.

The compounds II, III and IV in which the cation is a metal cation with valency m, are designated by compounds Ia, IIIa and IVa respectively. The cation can be a metal alkali cation, a metal earth alkaline cation, a transition metal cation, a trivalent metal cation, or a rare earth cation. Mention may be made of Li$^+$, Na$^+$, K$^+$, Cs$^+$, Ag$^+$, Cu$^+$, Mg$^{2+}$, Pt$^{2+}$, Pd$^{2+}$, Cd$^{2+}$, Co$^{2+}$, Cu$^{2+}$, Pb$^{2+}$, Zn$^{2+}$, Sn$^{2+}$, Rh$^{2+}$, Gd$^{3+}$, Sm$^{3+}$, Fe$^{3+}$, Ti$^{3+}$, Bi$^{3+}$, La$^{3+}$, Ho$^{3+}$, Sc$^{3+}$, Al$^{3+}$, Y$^{3+}$, Yb$^{3+}$, Lu$^{3+}$, Ru$^{3+}$, Eu$^{3+}$, Ce$^{4+}$, and Ti$^4$, as non limiting examples. An exhaustive list of cations, can be found in a periodic table or in "Basic Inorganic Chemistry, 3$^{rd}$ Edition, by Cotton, Wilkinson & Gaus, J. Willey & Sons (1994)".

Compounds Ia, IIIa and IVa in which the cation is an alkali metal cation, especially a Li$^+$ cation, are of particular interest for developing ion conductive materials, these compounds inducing ionic conduction properties in most of the organic liquid mediums or polymers even those having a very low polarity. The applications are important in the field of electrochemistry, particularly in primary or secondary generators, in supercapacitors, in fuel cells, in electroluminescent diodes, in electrochrome systems and in the sensors. These compounds can also induce antistatic properties in polymers, organic liquids or gels even those having low polarity, even at low concentrations.

Compounds IIa, IIIa and IVa in which the cation is selected from Li$^+$, Cs$^+$, Ag$^+$, Cu$^+$, Mg$^{2+}$, Pt$^{2+}$, Pd$^{2+}$, Cd$^{2+}$, Co$^{2+}$, Cu$^{2+}$, Pb$^{2+}$, Zn$^{2+}$, Sn$^{2+}$, Rh$^{2+}$, Gd$^{3+}$, Sm$^{3+}$, Fe$^{3+}$, Ti$^{3+}$, Bi$^{3+}$, La$^{3+}$, Ho$^{3+}$, Sc$^{3+}$, Al$^{3+}$, Y$^{3+}$, Yb$^{3+}$, Lu$^{3+}$, Ru$^{3+}$, Eu$^+$, Ce$^{4+}$, Ti$^4$ are particularly interesting as a catalyst in various chemical reactions. The lithium salts may be used for example in reactions providing opening of epoxy rings.

The compounds Ia, IIIa and IVa in which the cation is Eu$^{3+}$ are useful for the development of luminescents products. A compound Ia, IIIa and IVa can be dissolved in a polymer, particularly in an inorganic/organic hybrid polymer obtained by a sol-gel process.

The compounds Ia, IIIa and IVa in which the cation is Cu$^{2+}$ are interesting for polymerization/doping of electronic conductive polymers (e.g. polythiophene, polypyrrole, poly(3,4-ethylenedioxythiophene), poly(styrenesulfonate) (PEDOT) in organic solvents such as propylene carbonate.

Compounds II, III and IV in which the cation is a metallic cation with valency m, are designated by compounds IIb, IIIb and IVb respectively. They are particularly useful as catalysts for various reactions. For example a compound in which is the cation tetrakis(acetonitrile) palladium (II) is useful as a catalyst for a vinylic polymerization reaction.

For example, mention may be made of cations obtained from ferrocene, from titanocene, from zirconocene, from indenocenium, or from a metallocenium arene, and metal transition cations complexed by phosphine ligands having optionally a chirality. As examples of ligands, mention may be made of 2,2'-bis-1,1'-phosphanorbornadienyle (BIPNOR) and of 2,2'-bis(diphenylphosphino)-1,1'-binaphthyle (BINAP). Many other phosphines are described and available, especially from the Rhodia company (see www.rhodia-phosphines.com). Other suitable organometallic cations are cations which have one or more alkyl or aryl groups covalently attached to a metal atom or to a group of metal atoms, such as the methylzinc, phenylmercury, trialkyl-tin or trialkyl-lead cations. The organometallic cation may be part of a polymer chain and/or carry substituents, such as ionic groups which increases the solubility thereof in an organic or aqueous medium, particularly —SO$_3$—, —CO$_2$—, PO$_{32}$— or —SO$_2$N—SO$_2$CF$_3$ groups. Much literature on organometallics is available, especially for the catalysis applications, including asymmetric catalysis (see "Fu, Pure Appl. Chem., Vol. 74, No 1, p. 33-36, (2002)", "Tang & Zhang, Chem. Rev., 103, 3029-3069, (2003)", "Crépy & Imamoto, Topics in Current Chemistry, 229, 1-40, (2003)", "Noyori, Angew. Chem. Int. Ed., 41, 2008-2022, (2002)", "The Organometallic Chemistry of the Transition Metals, by R. Crabtree, Willey-Interscience (2005)", "Aspinall & Docherty, Speciality Chemicals Magazine, January/February 2005, 34-35", "Advanced Inorganic Chemistry, 6$^{th}$ Edition, by Cotton, Murillo & Bochmann, Willey-Interscience (1999)" and "Asymetric Catalysis in Organic Synthesis, by Ryoji Yonori, J. Willey and Sons: New-York (1994)". The arene-ferrocenium cations activated by an actinic energy source are useful especially for photoinitiated cationic polymerizations.

The compounds II, III and IV in which the cation is a nitrosonium cation are designated by compounds IIc, IIIc and IVc respectively.

Compounds IIc, IIIc and IVc are oxidizing agents They are particularly useful for doping of conjugated polymers (polythiophene, polypyrrole, PEDOT, . . . ) to which they confer a substantial electronic conductivity. They can also be used in chemical reactions such as nitrosylation (for example nitrosylation of aniline CH$_3$OC$_6$H$_5$ into CH$_3$OC$_6$H$_4$-4-NO), or for the production of NO complexes such as:

(C$_6$Et$_6$)Cr(CO)$_3$+NO.BFST→[(C$_6$Et$_6$)Cr(CO)$_2$(NO)] BFST+CO

Compounds II, III and IV in which the cation is H$^+$ or a hydroxonium cation are designated by compounds IId, IIId and IVd respectively.

Compounds IId, IIId and IVd have acidic properties and they can be used for the preparation of compounds having other cations, for example by reaction with a potassium carbonate in water, or with a lithium phosphate Li$_3$PO$_4$ in an organic solvent. The reaction of a compound IId, IIId or IVd with a dilithium salt of oxalic acid, in an organic solvent such as dimethylcarbonate, provides the lithium salt of compounds II, III or IV, respectively, where the insoluble lithium monoacid of oxalic acid can be removed by filtration.

Compounds IId, IIId and IVd are also useful to initiate cationic polymerization reactions, for example for the preparation of polysiloxanes, and as catalysts for example for Friedel & Crafts reactions.

Compounds II, III and IV in which the cation is an onium cation with at least one heteroatom such as N, O, S, I or P carrying a positive charge, are designated by compounds IIe, IIIe and IVe respectively. Mention may be made of hydroxyonium, oxonium, ammonium, amidinium, guanidinium, pyridinium, quinolinium, imidazolium, pyrazolium, imidazolinium, triazolium, sulfonium, phosphonium, phospholium, phosphorolium, iodonium, carbonium, pyridazinium, pyrimidinium, pyrrolidinium, thiazolium, oxazolium, uronium, thiouronium, pyrazinium, piperazinium, piperidinium, pyrrolium, pyrizinium, thiomorpholinium and morpholinium ions.

These particular compounds can be used in a number of various applications.

A compound IIe, IIIe or IVe can be used particularly:
- as a salt dissolved in a liquid, polymer or gel solvent, for example for the preparation of electrolytes for super capacitors or of electrostatics compositions. It can also be used in the form of ionic liquid (usually an ionic liquid means a salt the melting point thereof being less than 100° C., preferably less than 50° C. and more preferentially, which is liquid at room temperature), as non-volatile solvent useful for the preparation of ion conducting materials and in which it is possible to dissolve salts, such as lithium salts, and polymers for the preparation of liquid, plastic or gels electrolytes. These compositions are useful for electrochemical generators and electrochromic devices. Said compound can also be used to dissolve redox couples in particular for preparing organic photovoltaïc cells, or to dissolve salts of various metals in order to carry their electroplating.
- as a solvent for carrying out chemical reactions, polymerizations (petrochemical industry), catalysis (fine chemicals, pharmaceutical compounds), including the preparation of chiral products, and synthesis of metallic nanomaterials. The large scope for changing the chemical structure by selecting the substituents allows changing their properties and thus allows tuning their polarity, their viscosity, their density, their miscibility with organic solvents (especially for the biphasic systems) and their chirality;

as a cleaning agent in the chemical, pharmaceutical or microelectronic industry, thanks to its good solvatation properties;

as a heat conducting fluid and as lubricant without any vapour tension, including lubrication of micro-electromechanics (MEMS), thanks to its thermal stability.

A compound II, III and IV which bears polymerizable or condensable groups can be used to form a polymer or it can be incorporated into a polymer matrix, in particular by reactions of grafting or by copolymerization This possibility is particularly useful for preparing antistatic compositions or gel membranes An important family of onium salts consists of cationic dyes such as cyanines, for example the 3,3'-diéthylthiatricarbocyanine responding to the formula

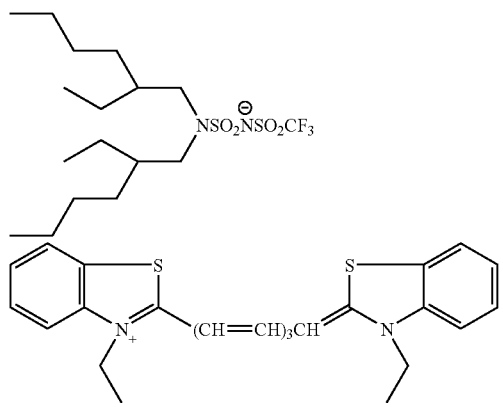

A numerous literature on ionic liquids obtained from onium salts is available. Mention may be made particularly of Seddon & al [Clean Products and Processes 1, (1999), 223-226], and Chauhan & al [Tetrahedron, 61, (2005), 1015-1060], Shreeve & al [Eur. J. Inorg. Chem., (2005), 2573-2580].

Among onium cations, mention may be made of $R_3O^+$ (oxonium), $NR_4^+$ (ammonium), $RC(NR_2)_2^+$ (amidinium), $C(NR_2)_3^+$ (guanidinium), $C_5R_6N^+$ (pyridinium), $C_3R_5N_2^+$ (imidazolium), $C_3R_7N_2^+$ (imidazolinium), $C_2R_4N_3^+$ (triazolium), $SR_3^+$ (sulfonium), $PR_4^+$ (phosphonium), $IR_2^+$ (iodonium), $(C_6R_5)_3C^+$ (carbonium), $C_4R_{10}N^+$ (pyrrolidinium), $ROC(NR_2)_2^+$ (uronium), $RSC(NR_2)_2^+$ (thiouronium), $C_3ONR_4$ (oxazolium), $C_3SNR_4$ (thiazolium), $C_4R_5N_2^+$ (pyrimidinium), $C_3R_5N_2^+$ (pyrazolium), $C_4R_5N_2^+$ (pyridazinium), $C_4R_5N_2^+$ (pyrazinium), $C_4R_{10}N_2^{2+}$ (piperazinium), $C_5R_{11}N^+$ (piperidinium), $C_4R_5N^+$ (pyrrolium), 1,4-Diazoniumbicyclo[2,2,2]Octane $(C_6R_{14}N_2^{2+})$ and $C_4R_9N^+$ (morpholinium).

In an onium cation, radicals R are identical or different, and they may be chosen from H, F and the following groups:
  alkyl, alkenyl, oxa-alkyl, oxa-alkenyl, azaalkyl, azaalkenyl, thiaalkyl, thiaalkenyl, silaalkyl, silaalkenyl, aryl, arylalkyl, alkylaryl, alkenylaryl, dialkylamino and dialkylazo groups;

cyclic or heterocyclic groups possibly including at least one lateral chain including heteroatoms such as nitrogen, oxygen, sulphur;
  cyclic or heterocyclic radicals possibly including heteroatoms in the aromatic ring;
  groups comprising several aromatic or heterocyclic condensed or not condensed rings, possibly containing at least one atom of nitrogen, oxygen, sulfur or phosphorus;
  groups carrying an ionic function such as —OH, —SH, —COOH, —PO$_3$H$_2$, —NH$_2$, —CONH$_2$, —CONH—, —SO$_2$H, —SO$_3$H, —SO$_2$NH$_2$, and their salts;
  groups carrying —C(=O)—, —S(=O)—, —S(=O)$_2$—;
  groups carrying polar groups such as —CN or —NO
  groups carrying organometallic complexes;
  halogenated groups;
it being understood that when an onium cation carries at least two different radicals R other than H, these radicals can form a ring which is aromatic or not, possibly including the center bearing the cationic charge.

The onium cation may be in the form of an independent cationic group which is only linked to the anion by the ionic bond between the positive charge of the cation and the negative charge of the anion, said cationic part optionally being part of a repeat unit of a polymer.

Compounds II, III or IV which have an ammonium cation are useful particularly as an ionic liquid, as a solvent, as salts for ionic conduction materials, as a lubricant and as a catalyst. As examples of ammonium cations, mention may be made of tetrabutylammonium, N,N-diethyl-N-methyl-N-(2-methoxyethyl)-ammonium, N,N-diethyl-N-methyl-N-(2-methoxymethyl)ammonium, N,N-diethyl-N-methyl-N-(2-hydroxyethyl)ammonium, N-methyl-N,N,N-triethylammonium, N,N-diethyl-N-methyl-N-(2-methacryloxyethyl)ammonium, N,N-diethyl-N-methyl-N-(2-acryloxyethyl)ammonium, N,N-dimethyl-N-ethyl-N-(2-methoxy-ethyl)ammonium, N,N-dimethyl-N-ethyl-N-(2-hydroxyethyl)ammonium, N,N-dimethyl-N-ethyl-N-(2-methacryloxyethyl)ammonium, N,N-dimethyl-N-ethyl-N-(2-acryloxyethyl)ammonium, N,N-dimethyl-N-octyl-N-(2-hydroxyethyl)ammonium, N,N-diethyl-N-methyl-N-(2-methacryloxyethyl)ammonium, N,N-diethyl-N-methyl-N-(2-acryloxyethyl)ammonium, N-methyl-N-hexyl-N,N-diethylammonium, N,N-methyl-N-benzyl-N,N-tetradecylammonium, N,N-methyl-N-octyl-N-2-hydroxyethylammonium, N,N,N-trimethyl-N-3-hydroxypropylammonium, N,N,N-tris(2-hydroxyethyl)-N-methyl ammonium, N-butyronitrile-N,N,N-trimethylammonium, N,N,N-tris(2-ethylhexylamine)-N-propylammonium, N,N-diallyl-N,N-di-methylammonium, N,N,N,N-tetraallylammonium, as well as the following cations:

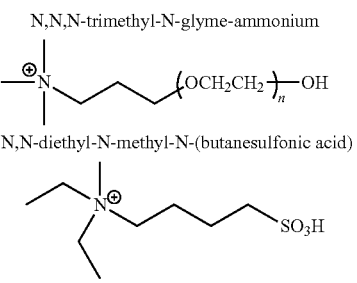

-continued

N-(2-acryloyloxyethyl)-N,N,N-trimethylammonium 1,4-bis-(N,N-dimethyl-N-methaloxyethylammonium (1R,2S)-N-methylephedrine-N,N-methyl-N-butylammonium

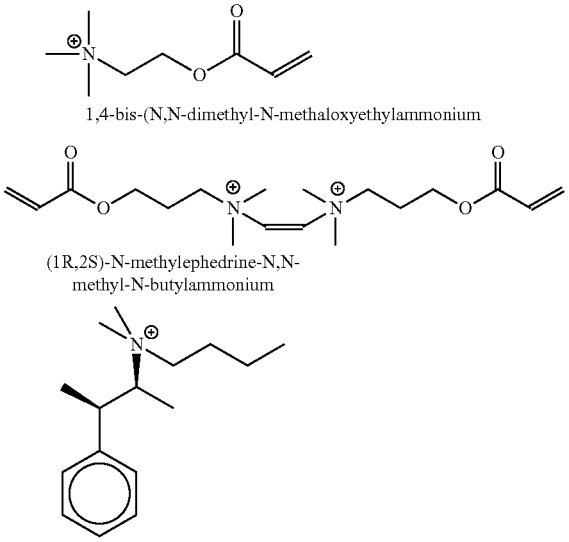

Compounds II, III or IV which have an imidazolium cation are useful particularly as an ionic liquid, as a solvent, as salts for ionic conduction materials, as a lubricant and as a catalyst. As examples of imidazolium cations, mention may be made of 1-ethyl-3-methyl-imidazolium, 1-butyl-3-methyl-imidazolium, 1-hexyl-3-methyl-imidazolium, 1-butyl-2,3-dimethyl-imidazolium, 1-methyl-3-(2-hydro-ethyl)imidazolium, 1-ethyl-3-(12-mercaptododécyl)imidazolium, 1-allyl-3-méthylimidazolium, as well as the following cations:

poly(1,3-hexyl-)imidazolium 1-butyl-3-(butanesulfonic acid)imidazolium 1-methyl-3-(3,3,4,4,5,5,6,6,7,7,8,8,8-tridecafluorooctyl)imidazolium 1-(L-2-ethylpyrolidine)-3-butylimidazolium the following ruthenium complex

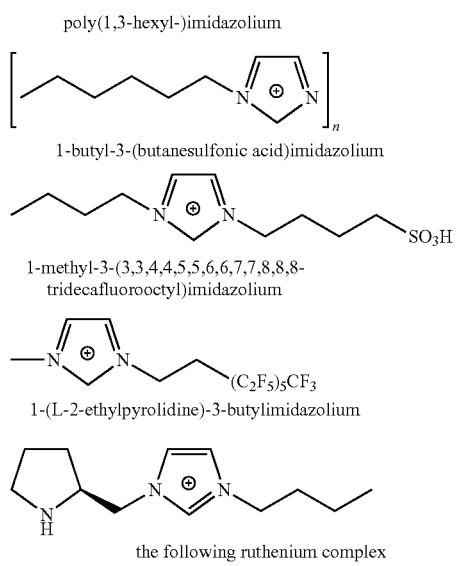

Compounds II, III or IV which have a phosphonium or sulfonium cation are useful as an ionic liquid, as a solvent, as salts for ionic conducting materials, as a lubricant and as a catalyst. The appropriate iodonium and sulfonium compounds are useful as photoinitiators for polymerization reactions. As examples of phosphonium, iodonium or sulfonium cations, mention may be made of the following cations: diphenyliodonium, butoxyphenylphenyliodonium, tetra(n-butyl)phosphonium, tetra(1-butyl)phosphonium, diethylmethylsulfonium, methoxy-methylethylsulfonium, ethyl-di(methylamino)sulfonium.

Compounds II, III or IV which have a pyridinium cation are useful as an ionic liquid, as a solvent, as salts for ionic conducting materials, as a lubricant and as a catalyst. As examples of pyridinium cations, mention may be made in particular of: 1-hexylpyridinium, 1-Butyl-4-methylpyridinium, 1-Butyl-3-methylpyridinium, 1-butyronitrile-pyridinium, 1-methoxyethylpyridinium, 1-3-hydroxypropylpyridinium and 1-allylpyridinium.

Compounds II, III or IV which have an imidazolinium cation are useful as an ionic liquid, as a solvent, as salts for ionic conducting materials, as a lubricant, as a catalyst and as a polymerization initiator. As an example of imidazolinium cations, mention may be made of 2,2'-azobis[2-(2-imidazolinium-2-yl)propane.

Compounds II, III or IV which have a pyrrolidinium cation are useful in particular as an ionic liquid, as a solvent, as salts for ionic conducting materials, as 5a lubricant, and as a catalyst. As examples of pyrrolidinium cations, mention may be made of the following cations: N-ethylpyrrolidinium, N-methyl-N-propylpyrrolidinium, N-ethyl-N-propylpyrrolidinium, N-methyl-N-trifluoroethyl-pyrrolidinium, N-methyl-N-allylpyrrolidinium, N-methyl-N-ethylpyrrolidinium, N-methyl-N-propylpyrrolidinium, N-methyl-N-methoxy-2-methylpyrrolidinium, N-methyl-N-methoxy-2-ethylpyrrolidinium, N-methyl-N-trifluoroethylmethylpyrrolidinium, N-ethyl-N-(2-methacryloxyethyl)pyrrolidinium, N-methyl-N-(2-methacryl-oxyethyl)pyrrolidinium, N-methoxymethyl-N-(2-methacryloxyethyl)pyrrolidinium, and N-(2-acryloyl-ethyl)-N-methoxyethylammonium

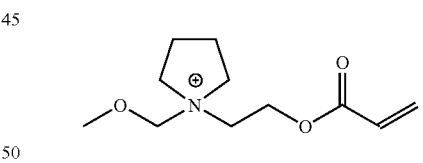

Other cations can be used for the compounds II, III and IV of the present invention. Mention may be made in particular of the compounds having the following formulae, in which groups $R_1$ to $R_6$ have the meaning given above for R.

Guanidinium

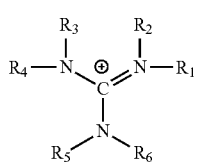 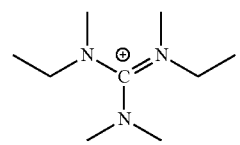

-continued

Amidinium

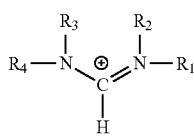 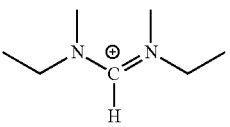

Thiouronium (X = S) or Uronium (X = O)

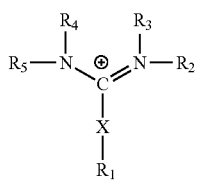 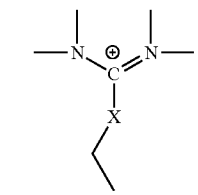

Pyridazinium

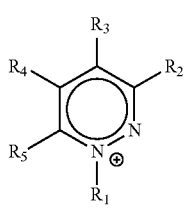 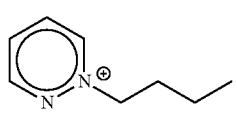

Thiazolium

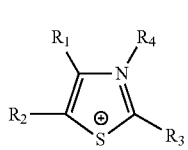 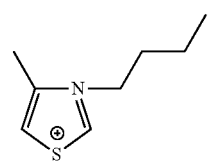

Oxazolium

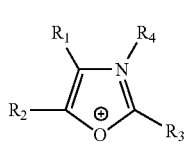 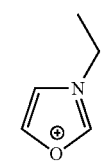

Pyrimidinium

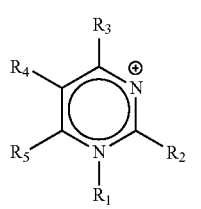 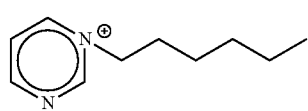

Pyrazinium

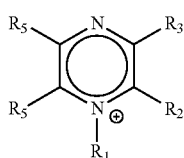 

-continued

Triazolium

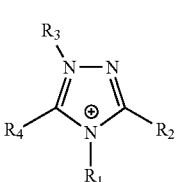 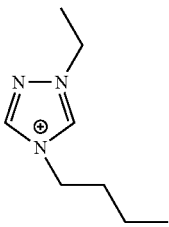

Pyrazolium

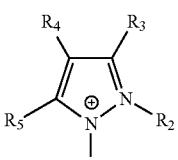 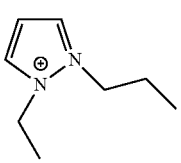

Imidazolinium

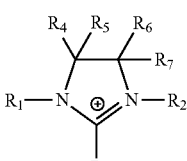 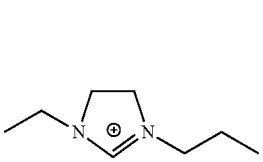

Benzoimidazolium

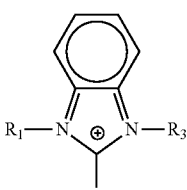 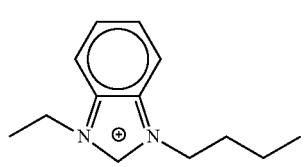

Isoquinolinium

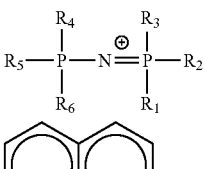

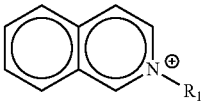

Electrolyte Solvant

Compounds II, III and IV of this invention in which the cation is an onium are particularly useful for preparing electrolyte solvants, which are another object of this application. These compounds in the molten state, also commonly referred to as ionic liquids, have both properties specific to organic solvents and ion conducting properties, because they consist of dissociated anions and cations.

They can thus be used directly as the electrolyte in a supercapacitor without requiring addition of another salt.

Another important aspect is the ability of these ionic liquids to dissolve other salts, especially metal salts, in particular lithium salts, to provide very conducive solutions. Similarly, ionic liquids or their mixtures with other metal salts are excellent solvents or platicizers for a large number of polymers, particularly those having polar or ionic functions. Both liquid compounds and polymers plasticized by ionic mixtures which behave as a solid electrolyte can be used in electrochemistry for primary or secondary generators, supercapacitors, electrochromic systems, antistatic coatings, or light-emitting diodes. The non-volatility of the ionic liquids of the invention, their thermal and electrochemical stability, and their enhanced conductivity are important parameters for the systems operating at low temperature and not having the usual flammability risks related to the use of usual organic solvents.

Ionic liquids of the invention are polar media of low volatility, and this property allows them to be used as a solvent for a great number of reactions in organic chemistry, such as nucleophiles and electrophiles substitutions, or anionic, cationic or radical polymerizations. It is further possible to dissolve catalysts in these ionic liquids, especially transition or rare earths metal salts optionally bonded by ligands, allowing to enhance catalytic properties. Examples of these catalysts include bipyridines, porphyrins, phosphines, arsines Organometallics such as metallocenes are also solutes that may have catalytic properties.

The non-volatility of the ionic liquids of the invention, their thermal stability and their non miscibility with non-polar solvents such as hydrocarbons, along with their hydrophobic character, are particularly advantageous to separate products of chemical reactions. It is also possible to operate in two-phase systems, the molten salt containing the catalyst and the reactive substrates being in solution in a hydrocarbon or in a non-miscible aliphatic ether. After the reaction, a simple decantation allows separation of the organic phase containing the reaction product and the molten salt which is purified by washing with a non solvent such as water or a hydrocarbon, and simply dried by vacuum.

In addition, ammonium, phosphonium and sulfonium cations can have an optical isomerism, and ionic liquids that contain them are chiral solvents which can promote the formation of enantiomeric excesses during the reactions carried out in these media. They can dissolve many other salts and control their properties, such as chirality, by the choice of substituents.

In addition, they can be used as a lubricant, thanks to their low vapour tension, their resistance to friction and to wear, an their thermal stability.

To carry out chemical catalysis, onium salts wherein the cationic center does not carry a proton which is potentially labile are generally preferred. The same is true in electrochemistry to avoid reduction of that proton. For other applications such as lubricants, quaternary ammonium compounds such as $[C_8H_{17}]_3NH$ have been considered. For this specific application, it may be interesting to mix the ionic liquid with particles of silica and carbon. Ionic liquids incorporating particles of silica or carbon are another object of the invention.

Compounds II, III and IV of this invention are particularly useful for the preparation of ion conducting materials, which are another object of the present application An ion conduction material of the present invention comprises an ionic compound of the invention in solution in a solvent. When the solvent is an electrolytic solvent, it may be an ion conduction material in itself, for example for supercapacitors or antistatics, but it can also serve as a solvent to dissolve an ionic compound, especially a lithium salt in lithium generators.

The solvent can be a liquid aprotic solvent, an electrolyte solvant, a polar polymer or mixtures thereof.

The aprotic liquid solvent is selected for instance from ionic liquids, linear éthers, cyclic éthers, esters, nitriles, nitrated derivatives, amides, sulfones, sulfolanes, alkylsulfamides and partially halogenated hydrocarbons. The particularly preferred liquid solvents are diethylether, dimethoxyethane, glyme, tetrahydrofurane, dioxane, dimethyltetrahydrofurane, methyl or ethyle formiate, propylene or ethylene carbonate, vinylidene carbonate, fluoroethylene carbonate, alkyl carbonates (in particular dimethyl carbonate, diethyl carbonate and methylpropyl carbonate), butyrolactones, acetonitrile, benzonitrile, nitromethane, nitrobenzene, dimethylformamide, diethylformamide, N-methylpyrrolidone, dimethylsulfone, tetramethylene sulfone and tetraalkylsulfonamides having 5 to 10 carbon atoms.

The electrolytic solvent can be chosen from compounds II, III or IV of the invention which have an ammonium, imidazolium, sulfonium, pyrrolidinium, phosphonium or pyridinium cation, particularly those which are liquid at room temperature and which have a cationic center not carrying a proton. In case of an imidazolium compound, it may be preferred to use an imidazolium in which the carbon between the two nitrogen atoms is alkylated, in particular in order to improve its stability versus a carbon electrode. The R groups may carry groups which are active in polymerisation, such as double bonds (for example acrylate, methacrylate, allyl, vinyl, vinylether, styrene, vinylester), epoxides, aziridines, or functions which are reactive in polycondensations (such as —NCO, —OH, —NH$_2$ and —COOH). If the cations have double bonds, they may be homopolymerised or copolymerised, for example with vinylidene fluoride, an acrylate, a maleimide, acrylonitrile, a vinylether, a styrene, etc. The epoxy groups can be polycondensed or copolymerised with other epoxy groups. These polycations are particularly useful (alone or in combination with a solvent, including an ionic liquid of this invention and/or one or more lithium salts or a mixture of lithium and potassium salts) as electrolyte in lithium batteries which have a lithium anode or a cathode inserting lithium at a low potential, such as titanium spinels or carbonaceous materials.

The polar polymer can be chosen from solvating polymers which are cross-linked or not, which bear grafted ionic groups or not. A solvating polymer is a polymer which comprises solvating units containing at least one heteroatom chosen from sulphur, oxygen, nitrogen and fluorine. As non limiting examples of solvating polymers solvants, mention may be made of: polyether having linear structure, comb or block structure, forming a network or not, based on poly(ethyleneoxide); copolymers containing ethylene oxide units or propylene oxide units or allylglycidylether units; polyphosphazenes; cross-linked networks based on polyethylene glycol crosslinked by isocyanates, and networks obtained by polycondensation and bearing groups that allow the incorporation of crosslinkable groups. Mention may also be made of block copolymers in which certain blocks carry functions that have redox properties. The use of a crosslinkable polymer improves the mechanical strength after crosslinking, and allow to obtain gels. The polymer can comprise onium groups bearing a function which can react during the crosslinking step.

When a polar polymer is not solvating, it is used as a solvent in admixture with an aprotic liquid as defined above. Examples of such a non solvating polar polymers are polymers that contain mainly units obtained from acrylonitrile, vinylidene fluoride, N-vinylpyrrolidone or methyl methacrylate. The proportion of aprotic liquid in the solvent can vary from 2% (corresponding to a plasticized solvent) to 98% (corresponding to a gelled solvent).

An ionically conductive material of the present invention may additionally contain at least one salt commonly used in the prior art for preparing an ionically conductive material, said salt being preferably selected from the perfluoroalcanesulfonates, bis(perfluoroalkylsulfonyl)imides, bis(perfluoroalkylsulfonyl)methanes, tris(perfluoroalkylsulfonyl)methanes, bis(fluorosulfonyl)imides, tetrafluoroborates, hexafluorophosphates, bis-oxalato-borates, difluoro-oxalatoborates, and $LiB_{12}H_xF_{12-x}$ (0<x<2).

Of course, an ionically conductive material of the invention may additionally contain the additives usually used with this type of material, for example mineral or organic fillers in the form of a powder or fibres.

An ionically conductive material of the invention may be used as an electrolyte in an electrochemical generator. It is therefore an object of the present invention to provide an electrochemical generator comprising a negative electrode and a positive electrode, separated by an electrolyte, wherein the electrolyte is an ionically conductive material as defined above.

According to a particular embodiment, such a generator comprises a negative electrode consisting of metallic lithium, or one of its alloys, optionally in the form of nanometric dispersion in lithium oxide, or of a double nitride of lithium and of a transition metal, or of an oxide with low potential having the general formula $Li_{4-x+3y}Ti_5O_{12}$ ($0 \leq x \leq 1$, $0 \leq y \leq 1$) possibly doped, in particular $Li_4Ti_5O_{12}$, or of an amorphous or crystallized tin oxide, or of carbon and carbonated products resulting from pyrolysis of organic materials.

According to another embodiment, the generator comprises a positive electrode selected from vanadium oxides $VO_x$ ($2 \leq x \leq 2.5$), $LiV_3O_8$, $Li_yNi_{1-x}Co_xO_2$ possibly doped ($0 \leq x \leq 1$; $0 \leq y \leq 1$), $Li_yNi_{1-x-z}Co_xMn_zO_2$ possibly doped ($0 \leq x, y, z \leq 1$), spinels of manganese $Li_yMn_{1-x}M_xO_2$ (M=Cr, Al, V, Ni, $0 \leq x \leq 0.5$; $0 \leq y \leq 2$), organic polydisulfides, FeS, $FeS_2$, ferric sulfate $Fe_2(SO_4)_3$, phosphates complex oxides having a $LiMM'PO_4$ olivine structure or a $Li_{3+x}(MM')_2(PO_4)_3$ Nasicon structure wherein:

M represents one or more transition metals, selected in particular from iron, manganese, vanadium and titanium;

M' represents one or more metals different from a transition metal, selected in particular from molybdenum, nickel, magnesium, chromium, cobalt, zirconium, tantalum, copper, silver, niobium, scandium, zinc and tungsten weight ratio metals M/metals M' being greater than 1;

the polyanions $PO_4$ may be substituted by $SiO_4$ and/or $SO_4$, and also substituted at a level lower than 5% by molybdenate, niobate, tungstate, zirconate or tantalate polyanions.

Olivines are selected preferably from $LiFePO_4$ materials.

According to another embodiment, the positive electrode material and/or the negative electrode material is coated with a carbon deposit, preferably obtained by pyrolysis of an organic precursor, especially titanates for negative electrodes and $LiMM'PO_4$ olivines and more particularly $LiFePO_4$ for the positive electrodes.

The collector of the positive electrode is preferably in aluminum.

A compound II, III or IV in which the cation is $Li^+$ can be used advantageously in an ion conducting material constituting the electrolyte and/or in an electrode material of a lithium battery.

The electrolyte of a lithium generator can be optimized, for example to provide high performance at low temperature, for example by use of solvent compositions containing methylbutyrate, methylpropionate, ethylpropionate, ethylbutyrate and ethyl-valerate (see Nasa Tech Briefs, December 2005), or to improve security through the use of fluorinated solvents such as methyltrifluoroethylcarbonate (see Nasa Tech Briefs, May 2002). It may also contain additives for example to improve the quality of the passivation layer of carbon anodes in Li-Ion batteries (vinylidene carbonate, . . . ), overcharging, stability of salts (see S. S. Zhang [Journal of Power Sources 162 (2006) 1379-1394]).

It was found interesting to prepare electrolytes using one of the salts of the invention, particularly LiBFST, in admixture with $LiPF_6$ and/or $LiBF_4$. The use of the salts of the invention as an additive to the electrolytes based on $LiPF_6$ improves the formation of the passivation layer on the carbon anode, the use of $LiPF_6$ and/or $LiBF_4$, particularly both, as additives to an electrolyte composition containing salts of the invention can improve performances, especially towards the aluminum current collectors. This issue may be important in batteries because of the overvoltage which can appear in the cathode during cycling.

A further object of the invention is thus an electrolyte which contains at least one compound II, III or IV and at least one other salt selected from $LiPF_6$ and $LiBF_4$, the compound of the invention being present in a weight ratio of 2 to 98%, preferably of 5 to 95%, and more particularly of 10 to 90%.

A compound II, III or IV in which the cation is an organic cation, for example a N-propane-N-méthylpyrrolidinium cation, or a N-methyl-N-methoxy-methylpyrrolidinium cation, is useful as the solvent of the electrolyte of a lithium battery.

A ion conducting material of this invention can also be used as an electrolyte in an electrical energy storage system of the supercapacitor type. Another object of this invention is therefore a supercapacitor using at least one carbon electrode with a high specific surface, including carbon in the form of nanotubes, or an electrode containing a redox polymer or a conjugated polymer. It is advantageous to use a conjugated polymer which has 3 oxidation degrees, and which is present in the two electrodes. An example of such a polymer is a derivative of phenyl-3-thiophene.

In addition to systems using two carbon electrodes with a high specific surface, it is possible to prepare a hybrid supercapacitor using a carbon electrode with high specific surface and a electrode capable of inserting alkaline cations, especially lithium. An advantageous embodiment is to use a carbon electrode with high specific surface, including that incorporating nanotubes as a positive electrode, and an electrode using lithium titanate $Li_4Ti_5O_{12}$ as the electroactive material.

In supercapacitors having two carbon electrodes with high specific surface, it is particularly advantageous to use ammonium cations (N,N,N,N-alkylated) or pyrrolidinium cations (N,N-alkylated), as a solution in a polar organic solvent and more particularly a carbonate (methylethylcarbonate, propylenecarbonate, diethylcarbonate). It is also particularly advantageous that these onium compounds contain at least one N-alkyloxyalkyl group, for example, to improve the solubility of these compounds. The choice of the onium compounds in the form of ionic liquids is also particularly judicious.

The ion conducting material of the present invention can also be used as the electrolyte in a light modulation system such as an electrochromic device including at least one electrochromic material. In such a system, the electrochromic material is advantageously placed on a layer of a semiconductor which is transparent in the visible spectrum, preferably a derivative of tin oxide or of indium oxide, on a glass substrate or a polymer substrate. Examples of preferred electrochromic materials include molybdenum oxide, tungsten oxide, titanium oxide, vanadium oxide, niobium oxide, cerium oxide, tin oxide, and mixtures thereof. The electrochromic material may be optionally dissolved in the electrolyte.

Compounds II, III and IV in which the cation is a cationic group having a —N=N— bond, a —N=N$^+$ bond, a sulfonium group, an iodonium group, or an arene-ferrocenium cation, substituted or not, possibly incorporated into a polymer frame, are interesting because they can be activated by heat or by an actinic energy source having the appropriate wavelength. As examples of such compounds, one can mention those in which the cation is a diaryliodonium cation, a dialkylaryliodonium cation, a triarylsulfonium cation, or a trialkylaryl sulfonium cation, a substituted or not substituted phenacyl-dialkyl sulfonium cation. The cations mentioned above may be part of a polymer chain.

The cation may include a group 2,2'[Azobis(2-2'-imidazolinium-2-yl)propane]$^{2+}$, 2,2'-Azobis[2-(5-methyl-2-imidazolinium-2-yl)propane]$^{2+}$, 2,2'-Azobis(2-methylpropionamidium)$^{2+}$, 2,2'-Azobis[2-(3,4,5,6-tetrahydropyrimidinium-2-yl)propane]$^{2+}$, 2,2'-Azobis{2-[1-(2-hydroxyethyl)-2-imidazolinium-2-yl]-propane}$^{2+}$ or 2,2'-Azobis(2-amidiniopropane)$^{2+}$. The compound of the invention is then capable of releasing, under the action of heat or of an ionizing radiation, radicals which enable initiation of polymerization or, cross-linking reactions or, in a general manner, chemical reactions involving free radicals. Moreover, these compounds are easily soluble in polymeric and monomeric organic solvents even of low polarity, in contrast to the derivatives of anions of the type Cl$^-$ usually associated with this type of compounds. On the other hand, they have a negligible vapour pressure contrary to the other radical initiators of the peroxide or azo type, which is a considerable advantage for the preparation of thin polymer films, the volatility of the initiator having as a consequence a bad polymerization or cross-liking of the surface of the film.

It has been noted that the strong dissociation of the ionic species of the compounds of the invention result in a stabilization of the carbocations, in particular those in which there is a conjugation with oxygen or nitrogen and, surprisingly in a strong activity of the protonic form of the compounds of the invention on certain monomers. It is also an object of the invention to provide for the use of the ionic compounds as photoinitiators which constitute sources of Brønsted acids, catalysts for the polymerization or cross-linking of monomers or prepolymers capable of cationic reaction, or as a catalysts for the modification of polymers.

The method for polymerizing or crosslinking monomers or prepolymers capable of reacting cationically is characterized in that a compound according to the invention is used as a photoinitiator source of an acid which catalyses the polymerization reaction. The compounds of the invention in which the cation is a group having a bond —N=N_ or —N=N$^+$, a sulfonium group, an iodonium group, or a substituted or non-substituted arene-ferrocenium cation, possibly incorporated in a polymeric network, are particularly preferred. (see Crivello [J. Polym. Sci. Part A: Polym. Chem., Vol 37, 1999], U.S. Pat. Nos. 6,008,267, and 6,008,265).

The choice of substituents is made in order to increase the solubility of said compound in the solvents used for the reaction of the monomers or prepolymers, and as a function of the desired properties for the final polymer. The monomers and polymers which may be polymerized or cross-linked by means of the photoinitiators of the present invention are those which may be subject to a cationic polymerization.

Among the monomers, those which include a cyclic ether function, a cyclic thioether function or a cyclic amino function, vinyl compounds (more particularly vinyl ethers), oxazolines, lactones and lactames may be mentioned.

Among cyclic ether or thioether type monomers, ethylene oxide, propylene oxide, oxetane, epichlorhydrin, tetrahydrofurane, styrene oxide, cyclohexene oxide, vinylcyclohexene oxide, glycidol, butylene oxide, octylene oxide, glycidyl ethers and esters (for example glycidyl methacrylate or acrylate, phenyl glycidyl ether, bisphenol A diglycidylether or fluorinated derivatives thereof), cyclic acetals having from 4 to 15 carbon atoms (for example dioxolane, 1,3-dioxane, 1,3-dioxepane) and spiro-bicyclo dioxolanes may be mentioned.

Among vinyl compounds, vinyl ethers constitute a very important family of monomers which are subject to cationic polymerization. By way of example, there may be mentioned ethyl vinyl ether, propyl vinyl ether, isobutyl vinyl ether, octadecyl vinyl ether, ethyleneglycol monovinyl ether, diethyleneglycol divinyl ether, butanediol monovinyl ether, butanediol divinyl ether, hexanediol divinyl ether, ethyleneglycol butyl vinyl ether, triethyleneglycol methyl vinyl ether, cyclohexanedimenthanol monovinyl ether, cyclohexanedimethanol divinyl ether, 2-ethylhexyl vinyl ether, poly-THF-divinyl ether having a weight between 150 and 5000, diethyleneglycol monovinyl ether, trirethylolpropane trivinyl ether, aminopropyl vinyl ether, and 2-diethylaminoethyl vinyl ether.

Other vinyl compounds may include by way of example 1,1-dialkylethylenes (for example isobutene), aromatic vinyl monomers (for example styrene, α-alkylstyrene, such as α-methylstyrene, 4-vinylanisole, acenaphthene), N-vinyl compounds (for example N-vinylpyrolidone or N-vinyl sulfonamides).

Among the prepolymers, there may be mentioned the compounds in which the epoxy groups are carried by an aliphatic chain, an aromatic chain, or a heterocyclic chain, for example glycidyl ethers or bisphenol A which are ethoxylated by 3 to 15 ethylene oxide units, siloxanes having lateral groups of the type epoxycyclohexene-ethyl obtained by hydrosilylation of copolymers of dialkyl, alkylaryl or diaryl siloxane with methyl hydrogenosiloxane in the presence of vinylcyclohexene oxide, condensation products of the type sol-gel obtained from triethoxy or trimethoxy silapropylcyclohexene oxide, urethanes incorporating reaction products of monovinylether butanediol and an alcohol of a function higher than or equal to 2 with an aliphatic or aromatic di or tri isocyanate.

The process of polymerization according to the invention consists in mixing at least one monomer or prepolymer capable of cationic polymerization and at least one ionic compound of the invention, and subjecting the mixture obtained to actinic or P radiation. Preferably, the reaction mixture is subjected to irradiation after having been shaped as a thin layer having a thickness lower than 5 mm, preferably in the form of a thin film having a thickness lower than or equal to 500 μm. The duration of the reaction depends on the thickness of the sample and the power of the source at the active wavelength λ. It is defined by the speed in front of the source, which is comprised between 300 m/min and 1 cm/min. Layers of final material having a thickness higher than 5 mm may be obtained by repeating many times the operation consisting of spreading a layer and treating it by irradiation.

Generally, the amount of photoinitiator used is between 0.01 and 15% by weight with respect to the weight of the monomer or prepolymer, preferably between 0.1 and 5% by weight.

An ionic compound of the present invention may be used as photoinitiator the absence of solvent, for example when it is intended to polymerize liquid monomers in which the ionic compound used as the photoinitiator is soluble or easily dispersible. This type of use is particularly interesting, since it permits to get rid of problems associated with solvents (toxicity, flammability).

An ionic compound of the present invention may also be used as photoinitiator in the form of a homogenous solution in a solvent which is inert towards polymerization, which solution is ready to use and easily dispersible, in particular in the case where the mixture to be polymerized or cross-linked has a high viscosity.

As an example of inert solvent, there may be mentioned volatile solvents, such as acetone, methyl-ethyl ketone and acetonitrile. These solvents will merely be used for diluting the products to be polymerized or cross-linked (to make them less viscous, especially when dealing with a prepolymer). They will be eliminated by drying after polymerization or cross-linking. Non-volatile solvents may also be mentioned. A non-volatile solvent is also used for diluting the products that are intended to be polymerized or cross-linked, and to dissolve the salt $A^+X^-$ of the invention used as photoinitiator, however, it will remain in the material formed and will thus act as a plasticizing agent. By way of example, propylene carbonate, γ-butyrolactone, ether-esters of mono-, di-, tri-ethylene or propylene glycols, ether alcohol of mono-, di-, tri-ethylene or propylene glycols, plasticizing agents such as phthalic acid esters or citric acid esters may be mentioned.

According to another embodiment of the invention, there is used as solvent or diluent a compound which is reactive towards polymerization, which has a low molecular weight and low viscosity and which will act simultaneously as a polymerizable monomer and as solvent or diluent for more viscous monomers or prepolymers used jointly. After the reaction, these monomers which have been used as solvents will be part of the macromolecular network finally obtained, their integration being greater when dealing with bi-functional monomers. The material obtained after irradiation is now free of products having a low molecular weight and an appreciable vapour tension, or susceptible to contaminate objects with which the polymer is in contact. By way of example, a reactive solvent may be selected from mono- and di-vinyl ethers of mono-, di-, tri-, tetra-ethylene and propylene glycols, N-methylpyrolidone, 2-propenylether of propylene carbonate which is commercially available for example under the designation PEPC from ISP, New Jersey, United States, and oniums bearing a polymerizable group.

To irradiate the reaction mixture, the irradiation may be selected from ultraviolet radiation, visible radiation, X-rays, γ rays and β radiation. When ultraviolet light is used as an actinic radiation, it may be advantageous to add to the photoinitiators of the invention photosensitizers intended to permit an efficient photolysis with wavelengths less energetic than those corresponding to a maximum of absorption of the photoinitiator, such as those emitted by industrial devices ($\lambda \approx 300$ nm with mercury vapour lamps in particular). Such additives are known, and by way of non-limiting example, there may be mentioned anthracene, diphenyl-9,10-anthracene, perylene, phenothiazine, tetracene, xanthone, thioxanthone, acetophenone, benzophenone, 1,3,5-triaryl-2-pyrazolines and derivatives thereof, in particular derivatives which are substituted on the aromatic nuclei by alkyl, oxa- or aza-alkyl radicals enabling among others to change the absorption wavelength. Isopropylthioxantone is a preferred example of photosensitizer when an iodonium salt according to the invention is used as a photoinitiator.

Among the various types of radiation mentioned, ultraviolet radiation is particularly preferred. On the one hand, it is easier to use than the other radiations mentioned above. On the other hand, photoinitiators are in general directly sensitive to UV rays and photosensitizers especially since the difference of energy ($\delta\lambda$) is lower.

The ionic compounds of the invention may also be used in association with initiators of radical types which are produced thermally or by the action of actinic radiation. It is thus possible to polymerize or cross-link mixtures of monomers or prepolymers containing functions in which the modes of polymerization are different, for example monomers or prepolymers which polymerize by free radical reaction and monomers or prepolymers which polymerize by cationic polymerization. This possibility is particularly advantageous for providing interpenetrated networks having different physical properties from those which would be obtained by a mere mixture of polymers originating from the corresponding monomers. The vinyl ethers are not or are very little active by radical initiation. It is therefore possible, in a reaction mixture containing a photoinitiator according to the invention, a free radical initiator, at least one monomer of vinyl ether type and at least one monomer comprising non-activated double bonds such as those of the allyl groups, to carry out a separate polymerization of each type of monomer. On the other hand, it is known that monomers which are deficient in electrons, such as esters or amides of fumaric acid, maleic acid, acrylic or methacrylic acid, itaconic acid, acrylonitrile, methacrylonitrile, maleimides and derivatives thereof, are formed in the presence of electron enriched vinyl ethers, charge transfer complexes which give alternating polymers 1:1 by free radical initiation. An initial excess of vinyl monomers with respect to this stoichiometry enables preservation of polymerizable functions by pure cationic initiation. Triggering of the activity of a mixture of free radical initiator and cationic initiator according to the invention may be carried out simultaneously for the two reactants in the case for example of isolation with actinic radiation of a wavelength in which the photoinitiators of the invention and the free radical initiators selected are active, for example $\lambda=250$ nm. By way of example of initiators, the following commercial products may be mentioned: Irgacure 184®, Irgacure 651®, Irgacure 261®, Quantacure DMB®, Quantacure ITX®.

It may also be advantageous to use the two types of polymerization in a sequential manner to form first prepolymers which are easy to produce and in which hardening, adhesiveness, solubility as well as cross-linking degree may be modified by initiating the activity of the cationic initiator. For example, a mixture of a thermo-dissociable free radical initiator and a cationic photoinitiator according to the invention enables to provide sequential polymerization and cross-linkings, first under the action of heat, then under the action of actinic radiation. In a similar manner, if a free radical initiator and a cationic photoinitiator according to the invention are selected, the first being photosensitive to wavelengths longer than the ones which initiate the photoinitiator according to the invention, there is obtained a cross-linking in two controllable steps. Free radical initiators may for example be Irgacure 651®, enabling initiation free radical polymerizations at wavelengths of 365 nm.

It is also an object of the invention to use ionic compounds of the invention for reactions of chemical amplification of photoresists for microlithography. During such a use, a film of a material comprising a polymer and an ionic compound of the invention is subject to irradiation. The irradiation causes the formation of the acid by replacement of the cation M with a proton, which catalyzes the decomposition or transformation of the polymer. After decomposition or transformation of the polymer on the parts of the film which have been irradiated, the formed monomers or the polymer which has been converted are eliminated and what remains is an image of the non-exposed parts.

Among the polymers which may thus be modified in the presence of a compound of the invention, there may be mentioned for example polymers containing ester groups or tertioalkyl arylether groups, for example poly(phthaldehydes), polymers of bisphenol A and a diacid, polytertiobutoxycarbonyl oxystyrene, polytertiobutoxy-a-methyl styrene, polyditertiobutylfiimarate-co-allyltri-methylsilane and polyacrylates of a tertiary alcohol, in particular tertiobutyl polyacrylate. Other polymers are described in J. V. Crivello et al, Chemistry of Materials 8, 376-381, (1996).

This invention is described in more details by the following examples, which are given for illustrative purposes only and to which the invention is not limited.

EXAMPLE 1

Preparation of HTCST 16.81 g (100 mmoles), 3-trifluoromethyl-5-mercapto-1,2,4-triazole (provided by Toronto Invention Chemicals Inc.) were added with agitation to 170 ml of an aqueous 10% NaCl solution, then chlorine gas was added under the surface of the liquid through a tube. The temperature was maintained between 0 and −5° C. with a salted ice bath. At the end of the chlorine absorption, evidenced by a balance between entering gas flow and leaving gas flow, the insoluble 3-trifluoro-methyl-5-chlorosulfonyl-1,2,4-triazole was isolated and partially dried.

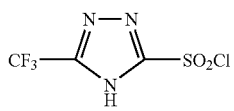

EXAMPLE 2

Preparation of HBCST 16.81 g (100 mmol) of 3-trifluoromethyl-5-mercapto-1,2,4-triazole (supplied by Toronto Research Chemicals Inc.) were added, with stirring, to 170 ml of a 10% aqueous solution of NaCl, and then chlorine gas was added under the surface of the liquid through a tube. The temperature was kept between 0 and −5° C. with an ice/salt bath. At the end of the chlorine absorption, demonstrated by an equilibrium of the gas streams entering and leaving, the insoluble 3-trifluoromethyl-5-chloro-sulfonyl-1,2,4-triazole was isolated and partially dried.

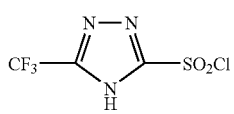

EXAMPLE 2

Preparation of HBCST 50 g of 3,5-dimercapto-1,2,4-triazole was synthesized starting from 2,5-dithiobiurea brought to reflux for 24 hours in water in the presence of two equivalents of NaOH (according to the process described in GB-1049053). The solution is subsequently acidified with HCl, the precipitate is filtered off and redissolved in water in the presence of NaHCO$_3$, and the solution is filtered and then acidified with HCl under an inert atmosphere. A precipitate of 3,5-dimercapto-1,2,4-triazole was thus recovered.

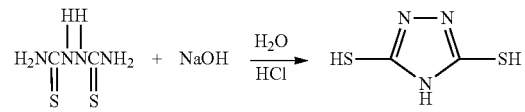

The protocol of example 1 was subsequently reproduced, replacing the 3-tri-fluoromethyl-5-mercapto-1,2,4-triazole with 3,5-dimercapto-1,2,4-triazole, and 3,5-dichlorosulfonyl-1,2,4-triazole was obtained.

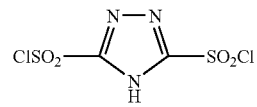

EXAMPLE 3

Preparation of Cl—SO$_2$-TrH—(CF$_2$)$_z$-TrH—SO$_2$Cl Compounds

Preparation of the dithiol HS-TrH—(CF$_\_$)$_z$-TrH—SH, z=2, 3, 4)

22.69 g (100 mmol) of tetrafluorosuccinyl chloride Cl(O=)CCF$_2$CF$_2$C(=O)Cl (supplied by SynQuest Labs.) were added slowly to a suspension of 18.23 g (200 mmol) of thiosemicarbazide (supplied by Aldrich) in 100 ml of dioxane containing 15.82 g (200 mmol) of pyridine. After stirring for 24 hours, the solvent was evaporated off and the product obtained was washed with water and then brought to reflux in 150 ml of a 10% aqueous solution of NaOH. After cooling, the reaction medium was acidified with HCl, and the product was recovered by settling out and then purified twice by sublimation under vacuum. The following compound was thus obtained:

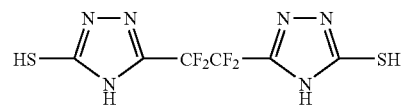

The protocol above was reproduced, replacing the tetrafluorosuccinyl chloride with 100 mmol of hexafluoroglutaryl chloride Cl(O=)CCF$_2$CF$_2$CF$_2$C(=O)Cl and with 100 mol of octafluoroadipoyl chloride (both provided by SynQuest Labs.), so as to obtain respectively the dithiols

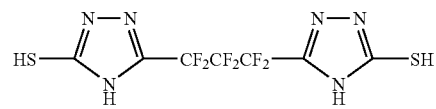

-continued

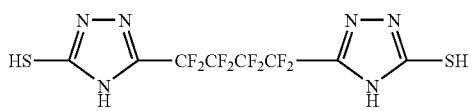

Preparation of $C_1$-$SO_2$-TrH—$(CF_2)_z$-TrH-$SO_2Cl$ Compounds

The protocol of example 1 was reproduced, using each of the dithiols obtained in the present example. The following compounds were obtained.

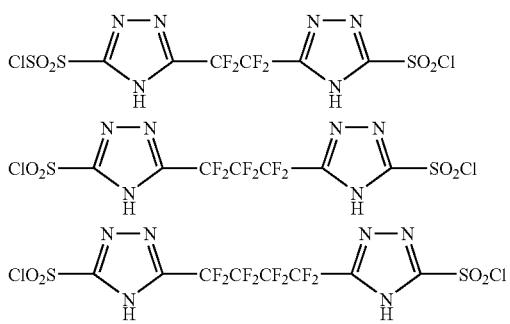

EXAMPLE 4

Preparation of $R_F$-TrH-$SO_2Cl$ Compounds

Preparation of $R_F$TrH—SH Thiols 23.25 g (100 mmol) of heptafluorobutyryl chloride $CF_3(CF_2)_2C(=O)Cl$ (supplied by SynQuest Labs.) were added slowly to a suspension of 9.11 g (100 mmol) of thiosemicarbazide (supplied by Aldrich) in 100 ml of dioxane containing 7.91 g (100 mmol) of pyridine. After stirring for 24 hours, the solvent was evaporated off, and the product obtained was washed with water and then brought to reflux in 150 ml of a 10% aqueous solution of NaOH. After cooling, the reaction medium was acidified with HCl, and the product was recovered by settling out and then purified by sublimation under vacuum. The following compound was thus obtained:

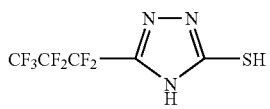

The protocol above was reproduced, successively replacing the heptafluoro-butyryl chloride with 100 mmol of nonafluoropentanoyl chloride, 100 mmol of tetrafluoropropionyl chloride, 100 mmol of 2,2-difluoroacetyl chloride and 100 mol of pentafluoropropionyl chloride, all the chlorides originating from SynQuest Labs. For the experiment with the last two chlorides mentioned, the reaction was carried out in a Parr reactor cooled to −20° C. during the addition of $HCF_2COCl$ and $C_2F_5COCl$, and then allowed to return to ambient temperature.

The following thiols were obtained:

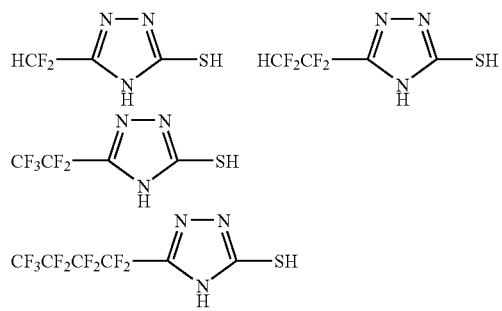

Preparation of $R_F$-TrH—$SO_2Cl$ Compounds

The protocol of example 1 was subsequently reproduced, replacing the 3-tri-fluoromethyl-5-mercapto-1,2,4-triazole successively with each of the $R_F$TrH—SH thiols above, and the following compounds were obtained:

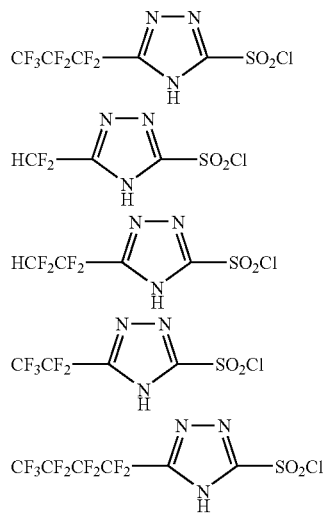

EXAMPLE 5

Preparation of Perfluorooxa Compounds

Preparation of Thiols 33.21 g (100 mmol) of undecafluoro-(2-methyl-3-oxahexanoyl) fluoride (supplied by SynQuest Labs.) were added, at ambient temperature for 1 hour, to a suspension of 9.11 g (100 mmol) of thiosemicarbazide in 100 ml of Freon®-113 (supplied by J. T. Baker). The mixture was subsequently brought to reflux for 4 hours and the solvent was then evaporated off. The product obtained was treated with an aqueous solution of ammonia until a neutral pH was obtained, and then the product was extracted with ether and then with Freon®-113. The product was subsequently separated by filtration and dried, and the solvent was then evaporated off. Undecafluoro-(2-methyl-3-oxahexanoyl)thiosemicarbazide was thus obtained. 0.3 mol of KOH in solution in 100 ml of water was added to 0.1 mol of this compound and the mixture was stirred at ambient temperature for 30 minutes, and then the medium was brought to reflux for 3 hours. After cooling, the medium was treated with a 10% aqueous solution of HCl until a pH of 4 was obtained, and the product was extracted with ether and then with Freon®-113. The product was subsequently separated by filtration and dried, and the solvent was then evaporated off.

The protocol above was reproduced, replacing the undecafluoro-(2-methyl-3-oxahexanoyl) fluoride with 100 mmol of perfluoro-2,5-dimethyl-3,6-dioxanonanoyl fluoride (supplied by SynQuest Labs.).

The following thiols were thus obtained:

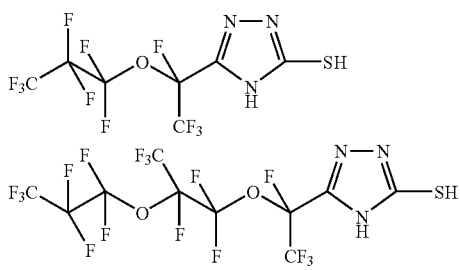

Preparation of Perfluorooxa Compounds

The protocol of example 1 was subsequently reproduced, replacing the 3-tri-fluoromethyl-5-mercapto-1,2,4-triazole successively with each of the two thiols above, and the following compounds were obtained:

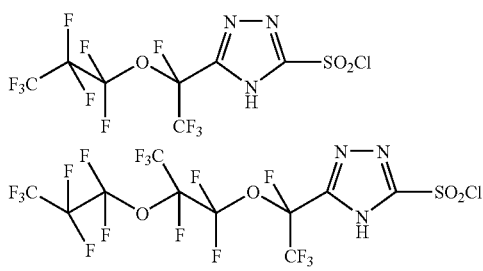

EXAMPLE 6

Preparation of MBCST 5.32 g (20 mmol) of HBCST (prepared according to the protocol of example 2) in 20 ml of anhydrous dichloromethane were brought to reflux for 24 hours with stirring in the presence of 1.17 g (20 mmol) of anhydrous NaCl, finely ground beforehand in a glovebox. After filtration, the sodium salt of 3,5-dichlorosulfonyl-1,2,4-triazole, NaBCST, was obtained.

The protocol above was reproduced, replacing NaCl with 4.85 g (20 mmol) of tetrabutylammonium chloride. The following products were thus obtained:

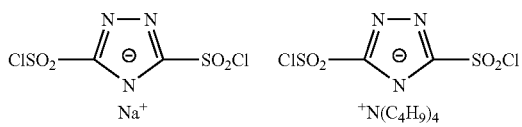

EXAMPLE 7

Compounds of
3-trifluoromethyl-5-fluorosulfonyl-1,2,4-triazole
(MTFST)

Potassium Salt KTFST

The 3-trifluoromethyl-5-chlorosulfonyl-1,2,4-triazole obtained in example 1 was dissolved in 85 g of dioxane and 28.24 g (300 mmol) of $KF \cdot H_2O$ were added. The medium was brought to reflux for 1 hour, and the solvent was then evaporated off. The solid residue was extracted in acetone and then the organic solution was evaporated, to give 24.18 g (yield of 94% with respect to $CF_3$-TrH-SH) of the potassium salt of 3-trifluoromethyl-5-fluorosulfonyl-1,2,4-triazole.

Melting point 154-157° C. (from dioxane).

$^{19}F$ NMR (acetone): $\delta=-62.4$ (s, 3F, $CF_3$), $\delta=62.5$ (s, IF, $SO_2F$) ppm.

$C_3F_4KN_3O_2S$ (257.21): calc. C, 14.01; H, 0.0; N, 16.34; S, 12.47; K, 15.20; measured C, 14.15; H, trace; N, 16.55; S, 12.47; K, 16.99.

The protocol above was reproduced, but by carrying out the exchange in water instead of dioxane, and the potassium salt of 3-trifluoromethyl-5-fluorosulfonyl-1,2,4-triazole was also obtained.

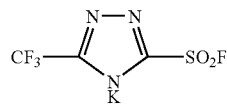

HTFST Compound 10 mmol of KTFST were mixed, by milling, with 30 mmol of ammonium hydrogen sulfate (Aldrich), and then the product was sublimated at 70° C. under vacuum in a sublimator equipped with a cold finger. The compound $CF_3$-TrH-$SO_2F$ was thus obtained.

Lithium salt LiTFST

According to a 1st protocol, an anhydrous solution of the lithium salt LiTFST in 10 ml of γ-butyrolactone (Tomiyama Pure Chemical Industries) was obtained by treating a solution of 10 mmol of KTFST (predried under vacuum at 130° C. for 24 hours) with 10 mmol of anhydrous $LiBF_4$ (Tomiyama Pure Chemical Industries), and then by eliminating, by filtration in a glovebox under argon, the $KBF_4$ formed.

In a 2nd protocol, the 1st protocol was reproduced, replacing the □-butyrolactone with acetonitrile. After evaporation and drying at 140° C. under vacuum for 24 hours, the dry LiTFST salt was obtained.

In a 3rd protocol, the 1st protocol was reproduced, but replacing 10 mmol of $LiBF_4$ with 10 mmol of anhydrous $LiNO_3$.

In a 4th protocol, an aqueous solution of the lithium salt LiTFST in 5 ml of water was obtained by treating a solution of 10 mmol of HTFST obtained by sublimation, with 5 mmol of $Li_2CO_3$.

In a 5th protocol, an anhydrous solution of the lithium salt LiTFST in 10 ml of a 3:7 ethylene carbonate (EC): dimethyl carbonate (DMC) solution (Ube Industries) was obtained, in a glovebox under argon, by adding, portion wise at 0° C. with stirring, 10 mmol of HTFST obtained previously by sublimation, to the EC:DMC solution containing 20 mmol of anhydrous oxalic acid lithium disalt. After filtration, the solution of LiTFST in EC:DMC was obtained.

Imidazolium Salt

The 2nd protocol described for LiTFST was reproduced, replacing 10 mmol of $LiBF_4$ with 10 mmol of 1-methyl-3-ethylimidazolium chloride (Aldrich), and 1-methyl-3-ethylimidazolium.TFST was obtained after filtration, evaporation of the acetonitrile and drying.

EXAMPLE 8

K 3,5-difluorosulfonyl-1,2,4-triazole (KBFST)

The protocol of example 7 was reproduced, replacing the 3-trifluoromethyl-5-fluorosulfonyl-1,2,4-triazole with the 3,5-dichlorosulfonyl-1,2,4-triazole prepared according to example 2, using 100 mmol of the compound of 2 and 600 mmol of $KF.H_2O$, and 23.06 g of the potassium salt of 3,5-difluorosulfonyl-1,2,4-triazole were obtained.

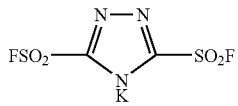

Yield 85% with respect to HS-TrH-SH.
Melting point 169-171° C. (from i-PrOH).
$^{19}F$ NMR (acetone): δ=62.3 (s, IF, $SO_2F$) ppm.
$C_7F_2KN_3O_4S_2$ (271.27): calc. C, 8.86; H, 0.0; N, 15.49; S, 23.64; K, 14.41; measured C, 8.61; H, 0.55; N, 15.33; S, 23.60; K, 16.71.

In the same manner as in the 2nd to 5th protocols of example 7, the acid form HBFST, the dry lithium salt LiBFST or the lithium salt LiBFST in solution in water, γ-butyrolactone, acetonitrile or 3:7 EC:DMC was obtained.

Imidazolium Salts 1-methyl-3-ethylimidazolium.BFST was obtained by reacting 10 mmol of 1-methyl-3-ethylimidazolium chloride (Aldrich) with 10 mmol of KBFST in 10 ml of anhydrous acetonitrile, by eliminating by filtration the KCl formed, by evaporating off the acetonitrile and by drying.

1-hexyl-3-methylimidazolium.BFST was obtained by treating 10 mmol of 1-hexyl-3-methylimidazolium chloride with 10 mmol of HBFST in 50 ml of water. After two hours with stirring, the medium was separated by settling out, 50 ml of water were added and the medium was then extracted with twice 20 ml of dichloro-methane. After evaporation and drying, the 1-hexyl-3-methylimidazolium-BFST salt was obtained.

EXAMPLE 9

The protocol of example 7 was reproduced for each of the triazole compounds bearing at least one fluorosulfonyl group, obtained in examples 3 and 5, in order to obtain the corresponding potassium salt.

Next, 10 mmol of potassium salt were mixed by milling with 30 mmol of ammonium hydrogen sulfate (Aldrich), and then the product was sublimated at 70° C. under vacuum in a sublimator equipped with a cold finger. The corresponding acid form was thus obtained, i.e. the following compounds:

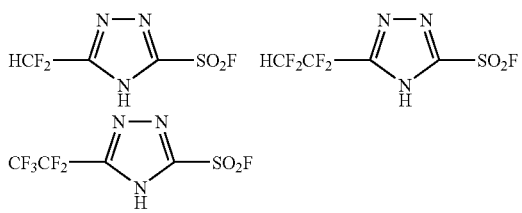

EXAMPLE 10

Compared Synthesis of HBFST and HFSI in HF

By way of comparison, the synthesis of bis(fluorosulfonyl) imide (HFSI) and of HBFST were carried out in anhydrous hydrofluoric acid.

Bis(chlorosulfonyl)imide HClSI was prepared by reacting, at reflux, 100 mmol of $ClSO_3H$ (Aldrich) with 100 mmol of $ClSO_2NCO$ (Aldrich) until there was no more change in $CO_2$, followed by distillation under vacuum.

In an autoclave, 1 g of bis(chlorosulfonyl)imide HClSI was reacted with 4 g of anhydrous HF, at various reaction temperatures and times. The particular conditions of each experiment and the $HN(SO_2F)_2$ yield obtained are summarized in the following table:

| Time (hours) | Temperature (° C.) | Yield (%) |
|---|---|---|
| 12 | 25 | 0 |
| 24 | 25 | 0 |
| 12 | 30 | 3-5 |
| 12 | 50 | 7-10 |
| 4 | 110 | 24 |
| 7 | 120 | 50 |
| 5 | 120 | 55 |
| 2 | 130 | 55 |

These results show that, even at temperatures of 130° C., the reaction yield does not exceed 55%. The product of the reaction contains in particular fluorosulfonic acid which comes from the decomposition of HClSI and which is difficult to separate on the industrial scale since it is necessary to use a distillation column with a high number of trays. In any event, the synthesis of HFSI with HF is not satisfactory.

The reaction was repeated, replacing 1 g of HClSI with 1 g of HBCST prepared according to the protocol of example 2. After 3 hours of reaction at 120° C., HBFST was obtained with a yield of 91% with good purity, the purification being carried out by a simple distillation.

The protocol above was reproduced, with LiF being added to the reaction medium, and the anhydrous LiBFST compound was obtained with good purity.

The protocol above was reproduced, using directly HBFST, prepared according to the protocol of example 8, instead of HCST, with LiF being added to the reaction medium, and the anhydrous LiBFST compound was obtained with good purity.

EXAMPLE 11

Synthesis of Compounds III

In a glovebox under argon, 18.3 g (150 mmol) of $CF_3CH_2ONa$, prepared beforehand in anhydrous THF by reacting trifluoroethanol with sodium trimethyl-silanoate, were added portion wise to 200 ml of anhydrous THF containing 13.3 g (50 mmol) of HBCST, prepared according to the process of example 2. After one hour, the solution was filtered in order to remove the NaCl precipitate formed, the solvent was then evaporated off, and the sodium salt of 3,5-di(1,1,1-trifluoro-2-ethanoxysulfonyl)-1,2,4-triazole (NaBTOST) was thus obtained.

By means of a similar process, the potassium salt was obtained by replacing $CF_3CH_2ONa$ with 150 mmol of $CF_3CH_2OK$, prepared in anhydrous THF by reacting trifluoroethanol with potassium trimethylsilanoate.

The products obtained correspond to the formulae below:

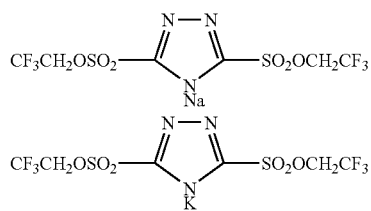

By means of a similar process, the sodium and potassium salts of 3,5-di(nonafluoropentanoxysulfonyl)-1,2,4-triazole (NaBNOST and KBNOST) were prepared by replacing 150 mmol of $CF_3CH_2ONa$ and $CF_3CH_2OK$ respectively with 150 mmol of $C_4F_9CH_2ONa$ and $C_4F_9CH_2OK$. The following products were thus obtained:

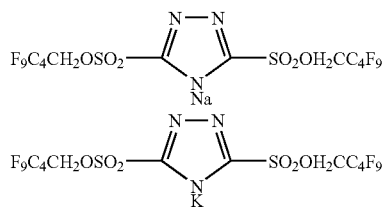

By means of a similar process, the sodium and potassium salts of 3,5-di(1,1,1,3,3,3-hexafluoro-2-propanoxysulfonyl)-1,2,4-triazole (NaBHOST and KBHOST) were also prepared by replacing 150 mmol of $CF_3CH_2ONa$ and $CF_3CH_2OK$ respectively with 150 mmol of $(CF_3)_2CHONa$ and $(CF_3)_2CHOK$. The following products were thus obtained:

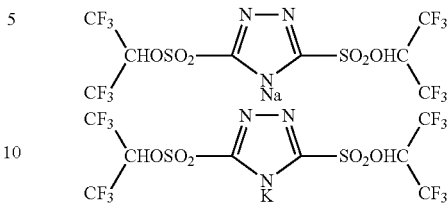

By means of a similar process, the sodium and potassium salts of 3-trifluoro-methyl-5-(1,1,1-trifluoro-2-ethanoxysulfonyl)-1,2,4-triazole (NaTHOST and KTHOST) were prepared by treating one equivalent of HTCST with two equivalents respectively of $(CF_3)_2CHONa$ and of $(CF_3)_2CHOK$. The following products were thus obtained:

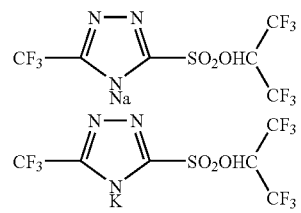

By means of a similar process, the sodium and potassium salts of 3-trifluoro-methyl-5-(1,1,1-trifluoro-2-ethanoxysulfonyl)-1,2,4-triazole (NaTTOST and KTTOST) were prepared by treating one equivalent of HBCST with two equivalents respectively of $CF_3CH_2ONa$ and of $CF_3CH_2OK$. The following products were thus obtained:

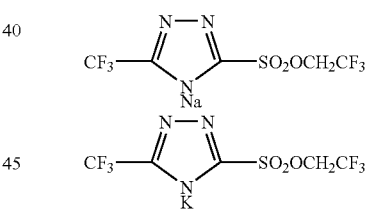

EXAMPLE 12

Polysalts

In a glovebox under argon, 26.61 g (100 mmol) of BBCST were reacted with 26.21 g (100 mmol) of 2,2,3,3,4,4,5,5-octafluoro-1,6-hexanediol (SynQuest Labs.), in 200 ml of an equivolume mixture of triethylamine/TUF. After 24 hours, the solution was filtered in order to remove the TEA.HCl precipitate formed, and then 200 mmol of $Li_2CO_3$ were added with stirring. After 4 hours, the solvent was evaporated off, and the product was taken up in acetonitrile and then filtered. After evaporation of the solvent, the polylithium salt LiPOOST was obtained.

By carrying out the process in the same manner, but using potassium carbonate in place of lithium carbonate, the polypotassium salt KPOOST was obtained.

The two polysalts correspond to the formulae

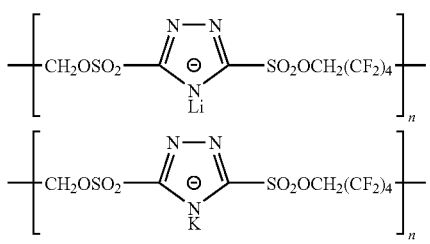

The protocol for the synthesis of LiPOOST was repeated, but using 50 mmol of 2,2,3,3,4,4,5,5-octafluoro-1,6-hexanediol and 50 mmol of 2,2,3,3,4,4-hexa-fluoro-1,5-pentanediol, instead of 100 mmol of hexanediol. The following random copolymer was thus obtained:

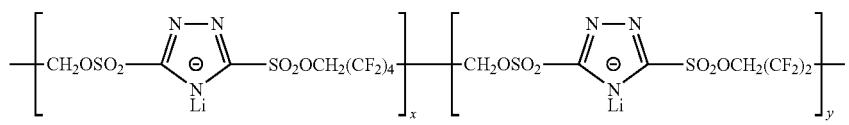

EXAMPLE 13

2,2'-azobis[2-(2-imidazolinium-2-yl)propane] TFST 5.14 g (20 mmol) of KTFST (prepared according to example 7) were solubilized in 20 ml of water. 3.23 g (10 mmol) of 2,2'-azobis[2-(2-imidazolinium-2-yl)propane]hydrochloride (Wako Pure Chemical) in solution in 20 ml of water were added with stirring. A precipitate was immediately formed, which was collected by filtration and then dried under vacuum. The 2,2'-azobis[2-(2-imidazo-linium-2-yl)propane]3-trifluoromethyl-5-fluorosulfonyl-1,2,4-triazole was recovered.

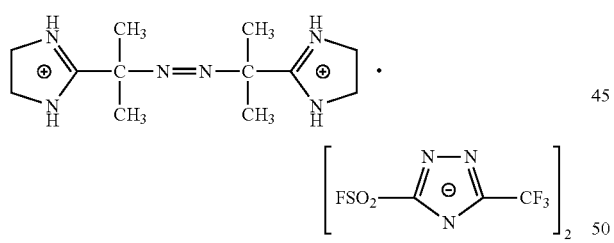

The protocol above was reproduced, replacing KTFST with 20 mmol of KBFST prepared according to example 8, and the following compound was obtained:

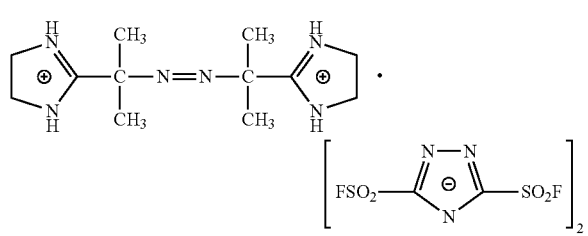

EXAMPLE 14

BFST.Nitrosonium 2.71 g (10 mmol) of KBFST (prepared according to the protocol of example 8) were solubilized in 10 ml of anhydrous nitromethane, and 1.17 g of nitrosonium tetrafluoroborate $NOBF_4$ (10 mmol, sold by Aldrich) were added in a glovebox. After one hour, the reaction medium was filtered in order to remove the insoluble potassium tetrafluoroborate, and a 1 M solution of BFST.NO in nitromethane was thus obtained.

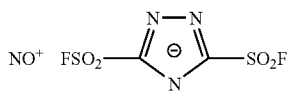

The protocol above was reproduced, replacing KBFST with 10 mmol of KTFST prepared according to example 7, so as to obtain a 1 M solution, in nitromethane, of the nitrosonium salt of 3,5-di(1,1,1-trifluoro-2-ethanoxysulfonyl)-1,2,4-triazole.

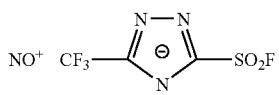

The protocol above was reproduced, replacing KBFST with 10 mmol of the potassium salt of 3,5-di(1,1,1-trifluoro-2-ethanoxysulfonyl)-1,2,4-triazole KBTOST prepared according to example 11, so as to give the nitrosonium salt

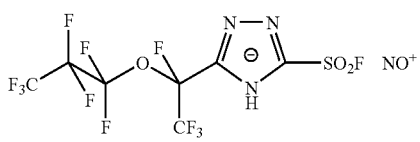

EXAMPLE 15

Sc.(BFST)$_3$ 1 mmol of anhydrous $ScCl_3$ (Aldrich) was introduced into 10 ml of anhydrous THF so as to obtain 1 mmol of the $ScCl_3(THF)_3$ complex. After stirring for 3 hours, 3 mmol of KBFST, prepared according to the process of example 8, were added and then the mixture was stirred for 24 hours. After removal of the KCl formed, by filtration, and evaporation and drying, the Sc(BFST)$_3$ salt was obtained.

This compound can be used as a catalyst, in particular for a Friedel-Crafts acylation, a Diels-Alder reaction and other reactions for the formation of C—C bonds. It can also catalyze the stereochemical polymerization of acrylates.

EXAMPLE 16

M$_2$+.(BFST)$_2$/M$_2$+.(BTOST)$_2$ M=Zn, Sn, Cu

In 100 ml of anhydrous THF, 10 mmol of Zn(BF$_4$)$_2$ hydrate (Aldrich), vacuum-dried beforehand, were reacted, for 48 hours with stirring, with 20 mmol of KBFST, prepared according to the process of example 8. After filtration in order to remove the KCl formed, evaporation and drying, the Zn(BFST)$_2$ salt was obtained.

The tin salt Sn(BFST)$_2$ and the copper salt Cu(BFST)$_2$ were prepared according to the same process.

The Zn(BTOST)$_2$, Sn(BTOST)$_2$ and Cu(BTOST)$_2$ salts were obtained according to the same process, replacing 20 mmol of KBFST with 20 mmol of KBTOST, prepared in example 11.

These salts are catalysts of various chemical reactions.

EXAMPLE 17

Organic Cation BFST and TFST Salts 23.31 g (100 mmol) of N,N-diethyl-N-methyl-N-(2-methoxyethyl)-ammonium tetrafluoroborate (DEMMOA, Kanto Chemical Co.) and 27.13 g (100 mmol) of KBFST prepared according to example 8 were added to 100 ml of anhydrous acetonitrile. After stirring for 30 min, the reaction medium was filtered and the solvent was evaporated off. The following compound (DEMMOA.BFST) was obtained in the form of a liquid:

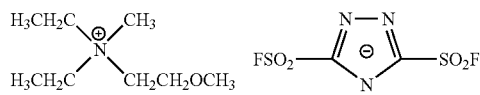

The liquid was subsequently dehydrated by bubbling dry argon for 24 hours at 60° C., and then finally with alumina until a water content <50 ppm was obtained.

By means of a similar process, the BFST salt of N-methyl-N-methoxymethylpyrrolidinium (MMOPyr) was obtained by replacing 100 mmol of DEMMOA chloride with 100 mmol of MMOPyr chloride. The MMOPyr chloride (MMOPyr.Cl) was obtained by reacting 100 mmol of 1-methylpyrrolidone (Aldrich) in solution in 100 ml of toluene, with 100 mmol of chloromethyl methyl ether (Aldrich) added slowly at 0° C., with stirring for 24 hours at ambient temperature, by evaporating off the solvent, by washing the product with toluene and acetone, and then by drying.

The MMOPyr-BFST compound obtained corresponds to the formula

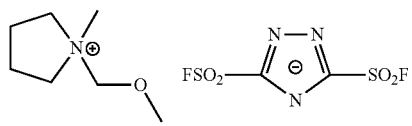

The DEMMOA.BFST and MMOPyr-BFST liquids obtained after dehydration exhibit a conductivity of greater than 1 mS·cm$^{-1}$. Their broad redox stability range makes them particularly advantageous electrolytes for electrochemical generators such as lithium batteries, supercapacitors, light-modulating systems and photovoltaic cells. They can also be used as solvents for carrying out chemical reactions or as antistatic agents.

The protocols above were reproduced, replacing 100 mmol of KBFST with 100 mmol of KTFST, with respectively DEMMOA.CL and MMOPyr.Cl. The following products were thus obtained:

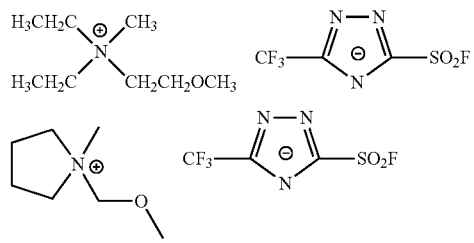

The protocols above were reproduced, replacing 100 mmol of KBFST with 100 mmol of KTTOST, prepared according to the process of example 11, with respectively DEMMOA.Cl and MMOPyr.Cl. DEMMOA.TTOST and MMOPyr.TTOST were thus obtained.

EXAMPLE 18

Compounds II with Onium Cation 100 mmol of a chloride A-Cl were reacted with 100 mmol of triazole derivative, in 50 ml of water, and then the aqueous phase was extracted with dichloromethane, the aqueous phase was dried, and then the dichloromethane was evaporated off. A salt was thus obtained in the form of a liquid.

The syntheses were carried out with various chlorides and various triazole derivatives, and they are summarized in the table below:

| Chloride of | Triazole | Compound obtained |
|---|---|---|
| 1-butyl-3-methylimidazolium | KBFST | BMIm•BFTST |
| 1-hexyl-3-methylimidazolium | KBFST | HMIm•BFST |
| 1-butyl-2,3-dimethylimidazolium | KBFST | BMMIm•BFST |
| 1-butyl-4-methylpyridinium | KTFST | MBPy•TFST |
| trihexyltetradecylphosphonium | KBFST | HTP•BFST |
| 1-methyl-1-octylpyrrolidinium | KTFST | MOPy•TFST |

EXAMPLE 19

Compounds II with Onium Cation 100 mmol of a precursor of the onium cation (PO) were reacted with 100 mmol of HBFST, in 50 ml of water. After evaporation, a compound of type II was obtained. The various syntheses are summarized in the table below.

| PO | Compound II |
|---|---|
| 4-(3-Butyl-1-imidazolio)-1-butanesulfonic acid | SBBIm-BFST |
| cytosine | Cytosinium-BFST |
| 1-methylimidazole | |
| 1-butylimidazole | |

EXAMPLE 20

Compounds II with Onium Cation 100 mmol of choline chloride (Aldrich) were reacted with 100 mmol of KBFST, in 50 ml of THF. After 2 hours with stirring, filtration, evaporation of the solvent and drying, the following compound was obtained:

A mixture of pyridine (100 mmol, Aldrich) and 4-chlorobutyronitrile $Cl(CH_2)_3CN$ (120 mmol, Aldrich) was stirred at 80° C. for 20 hours. After cooling, 500 ml of acetonitrile and 20 g of active carbon were added, and the medium was brought to 80° C. and then filtered. A product was precipitated by bringing the medium to 0° C., washed with three fractions of ethyl ether and then dried for 24 hours. The 1-butyronitrilepyridinium chloride below was obtained:

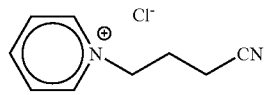

50 mmol of this chloride were then reacted with 50 mmol of KBFST, in 50 ml of THF. After 2 hours with stirring, filtration, evaporation of the solvent and drying, the following compound was obtained:

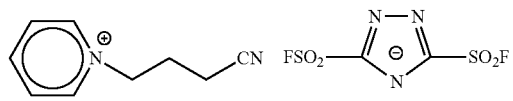

EXAMPLE 21

Polymerizable Onium Compounds 550 mmol of 1,4-dichloro-2-butene were added slowly to a solution, at 0° C., of 100 mmol of N,N-dimethylaminoethyle methacrylate (Ciba Speciality Chemicals) and 5 mmol of anthraquinone (Aldrich) in 50 ml of isopropanol, the reaction medium was stirred for 48 hours at ambient temperature and was then precipitated in 1 l of a 1:1 acetone/hexane mixture, and the following 1,4-bis(N,N-dimethyl-N-methaloxyethylammonium) chloride (denoted by $BDMAEMA.(Cl)_2$) was recovered by filtration:

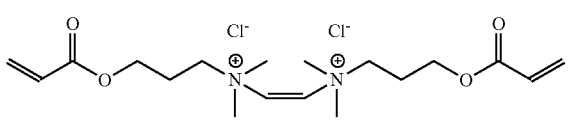

50 mmol of the $BDMAEMA.(Cl)_2$ compound and 100 mmol of KBFST were added to 200 ml of a 1:1 anhydrous THF/acetonitrile mixture. After 2 hours with stirring, the reaction medium was filtered in order to remove the KCl precipitate formed, and the solvent was evaporated off. The following $BDMAEMA.(BFST)_2$ compound was obtained:

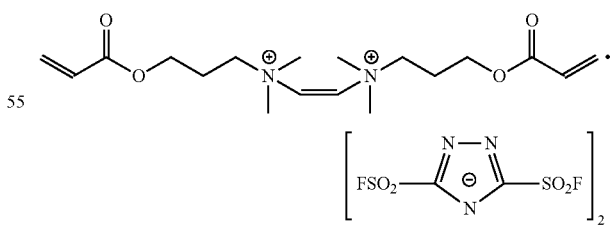

The process above was reproduced, reacting various onium halides (100 mmol) with the KBFST compound, so as to obtain compounds II having a polymerizable onium cation. The various syntheses are summarized in the table below.

| Halide | Cation | Final compound II |
|---|---|---|
| Onium-1·Cl (Kohjin Co., Ltd.) | N-(2-acryloyl-ethyl)-N,N,N-tri-methylammonium | 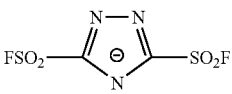 |
| Onium-2·Cl (Chemos GmBH) | diallyldimethyl-ammonium | 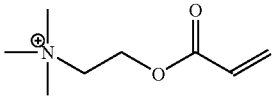 |
| Onium-3·Cl (Aldrich) | 1-Allyl-3-methyl-imidazolium | 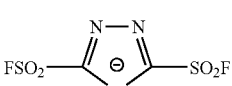 |
| Onium-4·Br (Aldrich) (a) | 1-Allylpyridinium | 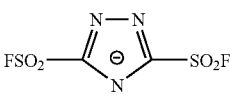 |

(a) removal of the KBr formed

By means of an analogous process, the BDMAEMA.(Cl)$_2$ compound and each of the onium-1 to 4 halides were reacted respectively with the KTFST, KBTOST and KTTOST compounds, using the same molar proportions.

The compounds of the present example, which each have a crosslinkable cation, are particularly advantageous for the preparation of antistatic coatings, in formulations for coatings, including formulations without volatile solvents, in adhesive formulations, including formulations without volatile solvents, for preparing polymer membranes or gels for electrochemical systems (batteries, supercapacitors, electrochromes or sensors), and for the production of resins for catalyzing chemical and/or electrochemical reactions.

For example, the onium-2 forms bis(3,5-methylene)dimethylpyrrolidinium units by radical-initiated cyclopolymerization. It gives, in addition to the homopolymers, copolymers with styrene, maleic anhydride, N-maleimides, vinylidene fluoride, acrylonitrile, methacrylonitrile, methyl methacrylate, with ω-methoxyoligo ethylene glycol acrylates or methacrylates having a mass of between 200 and 2000 daltons, optionally crosslinked with an α,ω-oligo ethylene glycol diacrylate or methacrylate.

EXAMPLE 22

Preparation of Polyoniums 20 g of a 25% aqueous solution of poly(diallyldimethylammonium chloride) of M, $2·10^5$ (Aldrich) were diluted in 100 ml of water. 10 g of KBFST in 100 ml of water were then added with stirring. The poly(BFST-diallyldimethylammonium) precipitate was subsequently washed with water and then dried. The following compound was obtained:

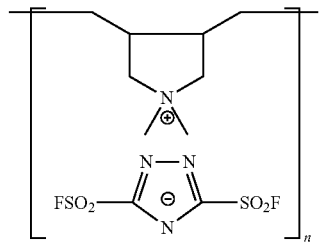

EXAMPLE 23

Diphenyliodonium Compounds 1.58 g (5 mmol) of diphenyliodonium chloride $(C_6H_5)_2ICl$ and 1.36 g of KBFST (5 mmol) were stirred together for 24 hours in acetonitrile. After removal of the KCl formed, by filtration, evaporation of the acetonitrile and drying, the diphenyliodonium 3,5-difluorosulfonyl-1,2,4-triazole salt was recovered.

The protocol above was reproduced, replacing the 5 mmol of KBFST with 5 mmol of KTTOST.

The two diphenyliodonium compounds obtained correspond to the following formulae:

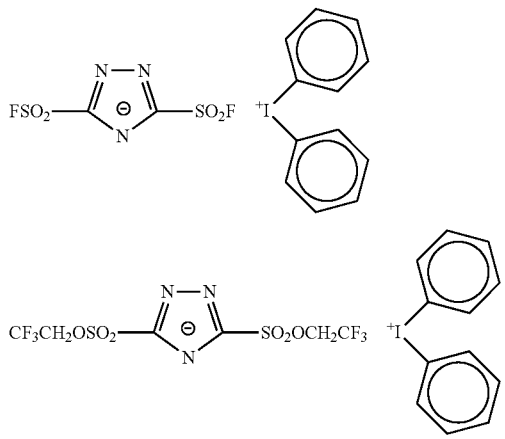

According to the same process, the iodonium salt of 3-($C_3F_7OCF(CF_3)$)-5-fluorosulfonyl-1,2,4-triazole was prepared by replacing 5 mmol of KBFST with 5 mmol of its potassium salt.

The protocol above was reproduced by reacting 5 mmol of KBFST or 5 mmol of KTTOST with 5 mmol of polyvinylphenyl-(4-butoxyphenyl)-4-iodonium methanesulfonate, and then removing the $CH_3SO_3K$ precipitate formed, so as to obtain respectively the BFST salt and the TTOST salt of polyvinylphenyl-(4-butoxyphenyl)-4-iodonium, which correspond to the following formulae:

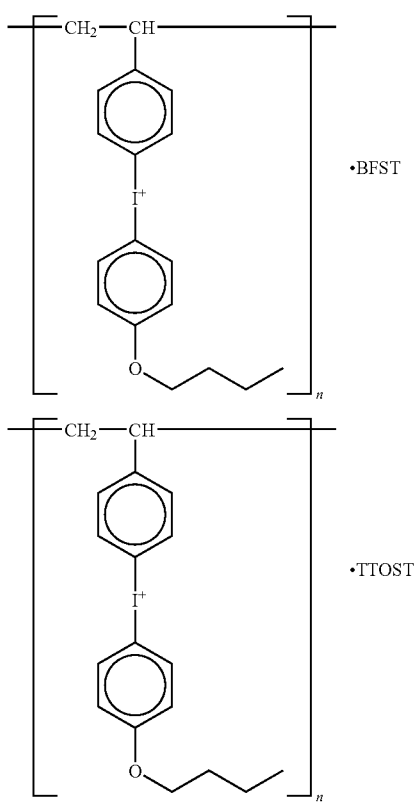

•BFST

•TTOST

The polyvinylphenyl-(4-butoxyphenyl)-4-iodonium methanesulfonate was prepared beforehand according to the process of example 1 of EP-0834502 8, by iodation of polystyrene, oxidation of the iodinated compound to iodosoacetate with the $CH_3CO_2H/(CH_3CO)_2O/H_2O_2$ mixture, and reaction with butoxybenzene in methanesulfonic acid.

The iodonium salts make it possible to initiate the reaction of cationic crosslinking of electron-rich monomers (vinyl ethers, alkyl vinyl ethers), under the effect of actinic radiation (light, γ-rays, electron beams).

They are soluble in most of the usual organic solvents (tetrahydrofuran, acetonitrile, dimethylformamide, ethyl acetate, glymes) and in aprotic solvating polymers such as poly(ethylene oxide). They are also soluble at more than 5% by weight in reactive solvents such as triethylene glycol divinyl ether.

The possibility of modifying the substituents of anions is an important element for optimizing photoinitiator formulations, in particular by adjusting the acidity of the acid generated (for example, HBFST is more acidic than HTFST, the —SO$_2$F group being more electron-withdrawing than CF$_3$), the solubility of the acid in the reaction medium, its volatility, its vapor pressure, the diffusion length and the catalytic activity.

The photoinitiating properties of these iodonium compounds were tested. For each of the compounds, a solution containing triethylene glycol divinyl ether and 1% by weight of iodonium compound was prepared, and the solution was irradiated with UV radiation at 254 nm, with a power of 1900 mW/cm$^2$. After a few seconds under irradiation, the reactive solvent set to a solid, this reaction being highly exothermic.

EXAMPLE 24

Dialkylphenacylsulfonium Compounds

In a 50 ml round-bottomed flask equipped with a magnetic stirrer and a reflux condensor, 1.99 g (10 mmol) of 2-bromoacetophenone (Aldrich), 1.6 g (10 mmol) of methyl-1-octyl sulfide (TCI America) and 2.55 g of NaBFST (10 mmol) were introduced into 20 ml of acetone. After having brought the reaction mixture to reflux for 20 min, the NaBr precipitate formed during the reaction was removed by filtration and the solvent was then evaporated off. S-methyl-S-1-octylphenacylsulfonium BFST was thus obtained, and was subsequently recrystallized from 2-propanol.

The phenacylsulfonium salt of 3-(1,1,1,3,3,3-hexafluoro-2-propanoxysulfonyl)-5-perfluorobutane-1,2,4-triazole was obtained according to the same process.

The sulfonium salts thus obtained correspond to the following formulae:

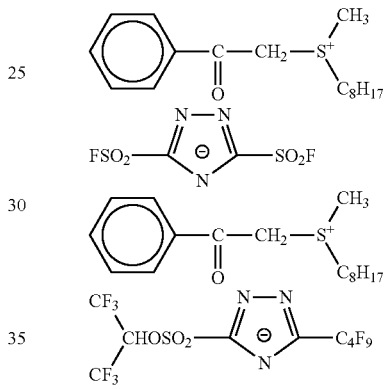

These compounds make it possible to initiate cationic photopolymerizations. They are soluble in many solvents, such as acetone, 2-butanone, chloroform and dichloromethane.

According to the same process, the S-methyl-S-1-octylphenacylsulfonium salt of 3-(C$_3$F$_7$OCF(CF$_3$))-5-fluorosulfonyl-1,2,4-triazole was prepared by replacing 5 mmol of KBFST with 5 mmol of its potassium salt.

EXAMPLE 25

Tetrakis(Acetonitrile)Palladium(II) BFST 2.22 g (5 mmol) of tetrakis(acetonitrile)palladium(II) tetrafluoroborate (CH$_3$CN)$_4$Pd(BF$_4$)$_2$, in 30 ml of tetrahydrofuran, were treated with 2.71 g of KBFST (10 mmol). After stirring for 24 hours, the reaction medium was filtered in order to remove the potassium tetrafluoroborate, KBF$_4$, precipitate and then the solvent was evaporated off. The 3,5-difluorosulfonyl-1,2,4-triazole salt of tetrakis-(acetonitrile)palladium(II) was obtained quantitatively.

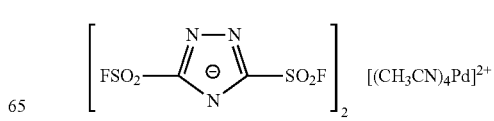

EXAMPLE 26

Chiral Anilinium BFST 100 mmol of N-methyl-N-ethylaniline (Aldrich) were quaternized with 100 mmol of bromopropane (Aldrich) at reflux in 100 ml of acetonitrile for 48 hours. After evaporation of the solvent, the N-propyl-N-methyl-N-ethylanilinium bromide (PMEA.Br) obtained was purified by washing with ether. 50 mmol of KBFST were added to 50 mmol of PMEA.Br in 100 ml of water, and then the solution was extracted with twice 50 ml of dichloromethane. After evaporation of the solvent and drying under vacuum, PMEA.BFST was obtained. The two optical isomer forms of this salt were separated on a chiral column. The two optical isomers isolated serve as a chiral reaction medium.

By means of a similar process, ethylmethyl sulfide (Aldrich) was quaternized with bromopropane, and then the BFST salt of diethylmethylpropyl-sulfonium was prepared. This salt was resolved into two optically active isomers, and it can be used to induce an enantiomeric excess in reactions for which it is used as a solvent.

EXAMPLE 27

PYR$_{13}$BFST 200 mmol of 1-methylpyrrolidone (Aldrich) in solution in 100 ml of toluene were quaternized with 100 mmol of diethyl sulfite (Aldrich), added slowly at 0° C., with stirring for 24 hours at ambient temperature. After evaporation of the solvent and drying, N-methyl-N-propylpyrrolidinium ethylsulfamate was obtained. 50 mmol of ethylsulfamate were solubilized in 50 ml of acetonitrile, and were reacted with 50 mmol of KBFFST. After stirring for 2 hours, and then filtration, evaporation of the solvent and drying, the N-propane-N-methylpyrrolidinium salt of 3,5-difluorosulfonyl-1,2,4-triazole (PYR$_{13}$BFST) corresponding to the following formula was obtained:

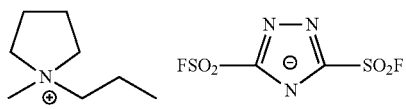

EXAMPLE 28

Polymerization Initiators

The 2,2'-azobis[2-(2-imidazolinium-2-yl)propane] TFST and BFST compounds prepared in example 13 are radical polymerization initiators which are soluble in most of the usual organic solvents (tetrahydrofuran, acetonitrile, dimethylformamide, ethyl acetate, glymes) and in aprotic solvating polymers, unlike 2,2'-azobis[2-(2-imidazolin-2-yl)propane] hydrochloride.

For each of the compounds of example 13, a solution, in acetonitrile, of one part of this initiator and of 100 parts of a polymer containing ethylenic unsaturations and obtained by polycondensation of polyethylene glycol having a mass of 1000 with 3-chloro-2-chloromethyl-1-propene, according to the procedure described by Alloin et al. (Solid States Ionics, (1993), 60, 3), was prepared. The viscous solution obtained was run onto a film of polypropylene (PP). After evaporation of the solvent, the film of polymer 110 μm thick on PP was stored for one week in a glovebox under argon in order to dry it. The crosslinking was then initiated by bringing the temperature of the film to 60° C. After an overnight period, a film having good mechanical properties and a low degree of extractable materials (less than 1%) was obtained. The solubility of the initiator used in the polymer matrix therefore makes it possible to obtain efficient and homogeneous crosslinking. Furthermore, this initiator is not volatile, unlike, for example, 2,2'-azobisisobutyronitrile, and the amount added can be best optimized for each type of polymerization.

The grafting on the unsaturated double bonds of the imidazoline-TFST salt, resulting from the reaction of the radical species formed during the decomposition of the —N═N— group, causes the polymer to have surfactant properties.

EXAMPLE 29

Polymer Doping

The nitrosonium compounds prepared in example 8 are particularly advantageous for the doping of conjugated polymers polythiophene, polypyrrole, etc.), on which they confer a noticeable electron conductivity.

For each of the compounds, a deposit of stereoregular poly(3-hexyl-thiophene) (sold by Aldrich) was carried out on a glass plate using a solution in chloroform. After drying, the deposit was doped with one of the compounds in solution in nitromethane. After doping, the poly(3-hexylthiophene) film obtained for each of the compounds exhibited an electron conductivity of greater than 1 S·cm$^{-1}$. These deposits are useful for the preparation of masks for the semiconductor industry.

Better stability of the conductivity during ambient-atmosphere aging of the films was noted with the 3-(C$_3$F$_7$OCF(CF$_3$))-5-fluorosulfonyl-1,2,4-triazole nitrosonium salt, probably because of the presence of hydrophobic fluorinated chains.

EXAMPLE 30

Photovoltaic Cell

An electrochemical photovoltaic cell of the type of that described in EP-718288-7 was prepared by assembling a system composed of two electrodes separated by an empty space 20 μm thick. The first electrode was coated with a nanoparticulate layer of titanium dioxide, TiO$_2$, at 0.28 μm thick, onto which cis-di(thiocyanato)bis(2,2'-bipyridyl-4,4'-dicarboxylate)ruthenium(I) was adsorbed as sensitizer. The space between the electrodes was filled with an electrolyte comprising the N,N-diethyl-N-methyl-N-(2-methoxyethyl) ammonium BFST obtained according to example 17, in which 10% by weight of methylhexylimidazolium iodide and 10 mmol of iodine have been dissolved beforehand. Under an illumination corresponding to 1/100 of standard solar illumination, an open-circuit voltage of 540 mV and a short-circuit current of 26 μA·cm$^{-2}$ are obtained.

An identical photovolatic cell in which the N,N-diethyl-N-methyl-N-(2-methoxyethyl)ammonium BFST compound of example 17 was replaced with the DEMMOA.TTOST compound of example 17 gave similar results.

EXAMPLE 31

Supercapacitor

Two electrochemical supercapacitors were prepared using the DEMMOA.BFST compound prepared according to example 17 as electrolyte in one, and the DEMMOA.TTOST compound of example 17 as electrolyte in the other. The electrodes, placed on a stainless steel disc, are 100 μm thick and are composed of activated carbon (MSP-20, Kansai Netsukagaku K. K.), of carbon (Denka Black HS100, Denki Kagaku Kogyo K. K.) and of a PVdF binder (PVdF900, Kureha) in a ratio by weight of 100:3:5. The electrodes were placed on either side of a 30 μm-thick cellulose separator and the whole was impregnated with one of the DEMMOA.BFST or DEMMOA.TTOST compounds, and then the complete system was sealed in a button cell case, in a glovebox. Good performance levels were obtained with these supercapacitors (more than 3000 charge/discharge cycles between 0 and 2.7 V for an energy density of greater than 5 Wh/kg and a maximum delivered power of greater than 3 kW/kg).

An identical supercapacitor in which the DEMMOA.TTOST compound of example 17 was replaced with a solution at 50% by weight of the N-methyl-N-methoxymethylpyrrolidinium BFST salt (MMOPyr.BFST) in an equivolume mixture of dimethylcarbonate/ethylmethylcarbonate, DMC/EMC, gave more than 3000 charge/discharge cycles between 0 and 2.7 V for an energy density of greater than 5 Wh/kg and a maximum delivered power of greater than 5 kW/kg.

EXAMPLE 32

Photoinitiators

The iodonium and sulfonium compounds prepared in examples 15 and 16 make it possible to initiate, under the effect of actinic radiation (light, γ-rays, electron beams), the reaction for cationic crosslinking of electron-rich monomers (vinyl ethers, alkyl vinyl ethers).

They are soluble in most of the usual organic solvents (tetrahydrofuran, acetonitrile, dimethylformamide, ethyl acetate, glymes) and in aprotic solvating polymers such as poly(ethylene oxide). They are also soluble at more than 5% by weight in reactive solvents such as triethylene glycol divinyl ether.

The photoinitiating properties of these compounds of examples 23 and 24 were tested by irradiating, with UV radiation at 254 nm, having a power of 1900 mW/cm², a solution of triethylene glycol divinyl ether containing them at 1% by weight. After a few seconds under irradiation, the reactive solvent set to a solid, this reaction being highly exothermic.

EXAMPLE 33

Catalysis

The compound of example 25 is useful as a catalyst for the vinylic polymerization of norbornene. The polymerization of norbornene at ambient temperature was carried out in nitromethane in the presence of 300 ppm of this salt. After 2 hours, the reaction medium was reprecipitated in methanol. Polynorbornene having a number-average mass of 230 000 was obtained with a yield of 68%.

EXAMPLE 34

Catalysis in Ionic Liquid Medium 2 mmol of 1-butyronitrilepyridinium.BFST, prepared according to the process of example 12, was treated with 1 mmol of PdCl₂ in 5 ml of dichloromethane. After stirring for 4 days, the solid was recovered by centrifugation, washed twice with 2 ml of dichloromethane, and then dried under vacuum, to give the following compound:

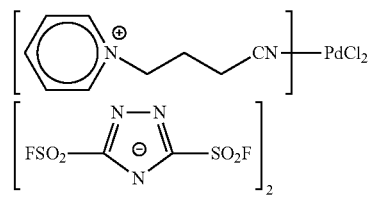

This product was used as catalyst for carrying out a Suzuki-type C—C coupling reaction according to the following protocol: 2.5 mmol of iodobenzene were added, in a round-bottomed flask, to 5 g of 1-butyronitrilepyridinium-BFST, followed by 2.75 mmol of boronic acid, 5.28 mmol of Na₂CO₃ and 2.5 ml of water, and finally 0.03 mmol of the PdCl₂ complex prepared beforehand. The mixture was heated at 110° C. with stirring for 12 hours, cooled, and then extracted with three times 15 ml of diethyl ether. The extracts were washed with salified water and then water, and finally dried with MgSO₄. The biphenyl synthesized was obtained with a yield of 86%, by filtering the medium and then evaporating off the solvent. The compounds of the invention are therefore effective as catalysts in these chemical reactions, and they are competitive with the anions already explored for this synthesis, in particular $(CF_3SO_2)_2N^-$ salts, which are expensive.

EXAMPLE 35

Diels-Alder Reaction Catalysis 1 mmol of yttrium bistrifluoromethanesulfonimidide (Aldrich) was added to 10 ml of 1-butyl-3-methyl-imidazolium.BFST. This medium was used for the catalysis of the Diels-Alder reaction of cyclopentadiene with methyl acrylate. Thus, 10 mmol of cyclopentadiene and 10 mmol of methyl acrylate were added to the reaction medium, which was then left at ambient temperature for two hours with stirring. The reaction products are extracted with hexane, the endo/exo ratio is 9:1. The catalyst can be re-used without loss of its activity.

EXAMPLE 36

Friedel-Craft Acylation Catalysis

In a glovebox under argon, 1 mmol of the copper salt Cu.(BFST)₂ obtained according to the process of example 16 and 20 ml of BMIm.BFST, prepared according to the process of example 18, were introduced into a round-bottomed flask, and then the medium was brought to 80° C. for 10 min in order to make it homogeneous. After cooling, 10 mmol of benzoyl chloride (Aldrich) and 50 mmol of anisole were introduced. The reaction medium was then brought to 80° C. for 8 hours, and then extracted several times with ether after cooling. The organic phase was washed with water, with aqueous NaHCO₃ and with a saturated aqueous solution of salt. After evaporation of the solvent, the product was purified by flash chromatography separation (eluant: 10/1 petroleum ether/ethyl acetate). The product below, mainly substituted in the para position, was thus obtained:

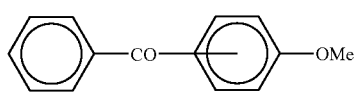

This reaction can also be carried out with the zinc and tin salts.

EXAMPLE 37

Catalysis of an Asymmetrical Michaelis Addition

A chiral cation of BFST was prepared using an imidazolium tetrafluoro-borate bearing an L-proline derivative as described in "Angew. Chem. Int. Ed. 2006, 45, 3093-3097", by reacting imidazolium.BF$_4$ in acetonitrile in the presence of KBFST. The following compound was obtained:

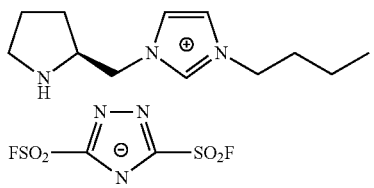

2.5 mmol of trans-β-nitrostyrene were then reacted, in 5 ml of cyclohexa-none, in the presence of 15 mol % of the BFST salt previously obtained and of 5 mol % of trifluoroacetic acid. After 8 hours at ambient temperature with stirring, the reaction medium was diluted with ether in order to precipitate the catalyst. The organic phase was separated and purified on a silica gel column, to give the following product with a yield of 98%:

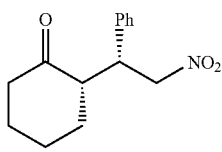

This compound exhibits a syn/anti ratio of 99:1 and an enantiomeric excess ee of 99%.

EXAMPLE 38

Preparation of a Suspension of Nanoparticles

In a glovebox under argon, 10 ml of BMIm.BFST, prepared according to the process of example 18, were introduced into a chemical reactor, and then 0.2 mmol of tris(dibenzylideneacetone)dipalladium(0) (Johnson Matthey Catalysts) was added, and the medium was stirred for 15 min at 30° C. The medium was then brought to 75° C. and hydrogen at 4 bar was introduced into the reactor. After 2 hours with stirring, a suspension of nanometric Pt particles of the order of 3 nm in size was obtained. These particles can be used to carry out catalysis reactions, for instance the hydrogenation of cyclohexane, or as a catalyst in fuel cell electrodes.

EXAMPLE 39

Ionic Liquid as Lubricant 100 mmol of 1-hexyl-3-methylimidazolium tetrafluoroborate and 100 mmol, respectively, of KBFST (3-SO$_2$F), KTFST (3-CF$_3$), KPFST (3-C$_2$F$_5$) and KIFST (3-C$_3$F$_7$), prepared according to the processes described in the previous examples, were reacted in 200 ml of THF. After 2 hours, the KBF$_4$ precipitate was removed, and the solvent was evaporated off, followed by drying under vacuum at 80° C. for 48 hours, so as to obtain the following products:

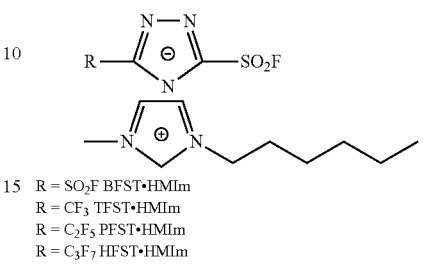

R = SO$_2$F BFST·HMIm
R = CF$_3$ TFST·HMIm
R = C$_2$F$_5$ PFST·HMIm
R = C$_3$F$_7$ HFST·HMIm

The tribological characteristics of the ionic liquids prepared according to the present example were determined using an Optimol SRV (Schwingung, Reibung, Verschleiss [reciprocating friction and wear]), in order to evaluate their friction and wear properties.

The friction coefficients for steel/aluminum contacts (SRV tester: load 50 N, frequency 25 Hz, amplitude 1 mm) are between 0.05 and 0.07.

The wear coefficients for steel/steel contacts (determined using an SRV tester: load 50 N, frequency 25 Hz, amplitude 1 mm) with a load of 200 N for 30 min, are between 0.05 and 0.066 $10^{-4}$ mm$^3$. For a load of 400 N, the wear coefficients are between 0.43 and 0.52.

Similar tests on steel/steel, steel/aluminum, steel/copper and steel/SiO$_2$ contacts confirmed the advantage of the products of the invention tested as a lubricant.

Supplementary tests with the oniums derived from the amine [C$_8$H$_{17}$]$_3$N (O$_3$N), O$_3$N$^+$H.BFST, O$_3$N$^+$H.TFST, O$_3$N$^+$H.PFST and O$_3$N$^+$H.HFST confirmed the advantage of the anions of the invention for this application.

EXAMPLE 40

Liquid Electrolyte

1 M solutions of KBFST and KTFST and also of their lithium salts LiBFST and LiTFST were prepared from their potassium salts by exchange with LiBF$_4$, as described in examples 7 and 8, in □-butyrolactone (Tomiyama Pure Chemicals) and in the 1:1 mixture by weight of EC/DMC.

These solutions were used as electrolyte and their conductivity was determined in a liquid conductivity cell coupled to an impedance spectrometer between 60 and −20° C. By comparison, the conductivity of solutions of salts of triflate, (CF$_3$SO$_2$)$_2$N, of PF$_6$ and of 3-trifluoromethyl-5-cyano-1,2,4-triazole (prepared according to the process described in EP-0 850 920 by cyanation of the diazonium of 3-trifluoromethyl-5-amino-1,2,4-triazole) was also determined. These electrolytes are prepared directly from their salts dissolved in the solvent. The results show in particular that:

the BFST salts have a conductivity equivalent to the TFSI salts,
the BFST and TFST salts have a conductivity which is much improved compared with that of the 3-trifluoromethyl-5-cyano-1,2,4-triazole, and even more improved compared with that of the CF$_3$SO$_3$ triflate salts.

It is thus possible to combine a simpler and less expensive chemistry than TFSI without loss of effectiveness.

EXAMPLE 41

Gel Electrolyte

An electrolyte was prepared by dissolving LiBFST in N-methyl-N-methoxymethylpyrrolidinium BFST (MMOPyr.BFST) at a concentration of 1 molar. A solution containing 60% by weight of this electrolyte and 40% by weight of poly(BFST.diallyldimethylammonium) (PDADMA.BFST) was then prepared in acetonitrile. The amount of solvent is adjusted so as to allow the solution to be spread in a thin film, in order to give, after drying, a thickness of 30 μm on a polypropylene film. The film thus obtained was dried with a stream of dry air, and then under a primary vacuum at 80° C. for 24 hours.

Similarly, a film of a ternary mixture LiTFSI (3M)/MMOPyr.BFST/PDADMA.BFST was prepared.

A binary gel electrolyte was also prepared using no LiBFST lithium salt in the composition of the electrolyte. This type of film can be used, for example, for preparing supercapacitors. The lithium salt can be subsequently introduced, for example, by placing this film side by side with a composite cathode containing a lithium salt.

These ternary electrolyte films are particularly advantageous for the preparation of thin-film electrochemical systems. They can be readily transferred to other supports by known film-transfer technologies.

These films can also be produced without the use of solvent, via an extrusion process.

The performance levels of these films can be readily optimized by those skilled in the art (conductivity, Tg, mechanical properties, etc.), for example by modifying the ratios of the various constituents, by changing the nature of the ionic liquid (anions, substituents, etc.), or by making mixtures of various salts, ionic liquids or polymers, in particular so as to decrease the eutectic melting point of the starting ionic liquid by mixing various ionic liquids.

EXAMPLE 42

Gel Electrolyte

A solution of 1-ethyl-3-methylimidazolium-BFST (EMI.BFST), LiBFST and a copolymer of ethylene oxide and of allyl glycidyl ether (5 mol %) was prepared in acetonitrile, and 1% by weight of Irgacure 651® (Ciba Speciality Chemicals) was added. The respective amounts of the three constituents are such that the following proportions are adhered to: 1 M LiBFST in EMI.BFST (40% by weight) and copolymer (60% by weight).

The solution in acetonitrile is run onto a polypropylene film, so as to obtain a film with a thickness of 20 μm after drying. Under argon sweeping, the film is subjected to UV radiation produced by a Hanovia® lamp, the maximum emission of which is at 254 nm, so as to initiate the polymerization of the allyl functions of the copolymer and to induce crosslinking thereof.

The crosslinked film constitutes an electrolyte which has excellent mechanical properties of the elastomer type. Ternary onium salt/lithium salts/polymer mixtures were obtained in a similar manner, with polyacrylonitrile, vinylidene fluoride homopolymer, copolymers of vinylidene fluoride with hexa-fluoropropene, vinylidene fluoride/tetrafluoroethylene/propylene terpolymers or poly(methyl methacrylate) as macromolecular material. Similarly, a film of a ternary mixture was prepared by replacing LiBFST with LiTFSI.

The performance levels of these films can be readily optimized by those skilled in the art (conductivity, Tg, mechanical properties, etc.), for example by modifying the ratios of the various components, by changing the nature of the oniums (anions, substituents, etc.) or by making mixtures of various salts, oniums or polymers.

EXAMPLE 43

Gel Electrolyte 15 g of a 4-branch polymer (Elexcel®-A210, DKS) were mixed with 4 g of LiBFST and 0.15 g of a photoinitiator, Perkadox® (Akzo-Nobel), and the mixture was run onto a polypropylene PP support. After a period of 5 seconds under a UV lamp giving off an energy of 10 mW, placed 6 inches away, a 25-μm crosslinked polymer film was obtained. This film was dried under vacuum at 80° C. for 24 hours and then dipped, in a glovebox under argon, for 5 minutes, in a container containing a mixture of 20 g of the mixture 1-hexyl-3-methylimidazolium.BFST and of propylene carbonate (90%: 10% by weight).

The polypropylene film detaches naturally from the polymer membrane. This membrane is a conductor of lithium cations via the LiBFST salt and has a greater optical transparency at 80° C. This membrane can be used for thin-film electrochemical systems, generators, electrochromic windows, sensors and supercapacitors. An improvement in the mechanical properties and in the transparency was demonstrated by adding a small proportion of fumed silica (Aérosil, Degussa) of the order of 1% by weight of the membrane, prior to the deposition/crosslinking of the salified 4-branch polymer film.

EXAMPLE 44

Gel Electrolyte

A mixture of diallyldimethylammonium.BFST (40% by weight), of N,N-diethyl-N-methyl-N-(2-methoxyethyl)ammonium.BFST (50% by weight), of tri-allyl isocyanurate (9.5% by weight) and of Esacure KT046 (Lamberti s.p.a, 0.5% by weight) was prepared. This mixture was then spread onto a polypropylene film with a thickness of 300 μm, coated with a polypropylene film, and then irradiated with a UV lamp with a power of 15 mW/cm$^2$, for 15 minutes. A gel electrolyte was thus obtained.

EXAMPLE 45

Antistatic Composition 20 mmol of the potassium salt of 3-$C_3F_7$OCF($CF_3$)-5-fluorosulfonyl-1,2,4-triazole (K$C_5F_{11}$OT), prepared according to the process of example 9, and 20 mmol of 1-butyl-3-methylimidazolium chloride (BMIm.Cl, Aldrich) were mixed in 100 ml of water. After stirring for 1 hour, the medium was extracted with 5 times 30 ml of dichloromethane, the $CH_2Cl_2$ phases were dried, and then the solvent was evaporated off.

According to the same process, 20 mmol of K$C_5F_{11}$OT were replaced with 20 mmol of 3-$C_3F_7$OCF($CF_3$)$CF_2$OCF($CF_3$)-5-fluorosulfonyl-1,2,4-triazole (K$C_8F_{17}O_2$T), prepared according to the process of example 9.

The following products were thus obtained:

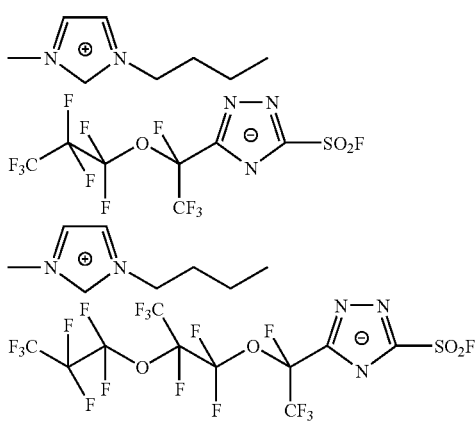

These products are particularly advantageous as antistatic agents, in particular for polymers. They can induce hydrophobic, water-repellent and anti-staining properties in the media in which they are dispersed (fibers, films, coatings, molded parts, extruded parts, etc.). The presence of the antistatic and hydrophobic properties on a cotton fabric which was soaked in a dilute solution of BMIm.$C_5F_{11}$OT in dichloromethane, and then dried, was thus noted.

EXAMPLE 46

Antistatic Composition 100 mmol of tri-2-ethylhexylamine were quaternized with 100 mmol of bromopropane (Aldrich) at reflux in 200 ml of toluene for 48 hours. After evaporation of the solvent, N,N,N-tri-2-ethylhexylamine-N-propylammonium bromide (TEHPA.Br) was obtained. The 3-perfluorobutyl-5-fluorosulfonyl-1,2,4-triazole salt of TEBPA was obtained by reaction of TEHPA.Br, in water, with the potassium salt of 3-perfluorobutyl-5-fluorosulfonyl-1,2,4-triazole, followed by extraction with dichloromethane. The following product was thus obtained:

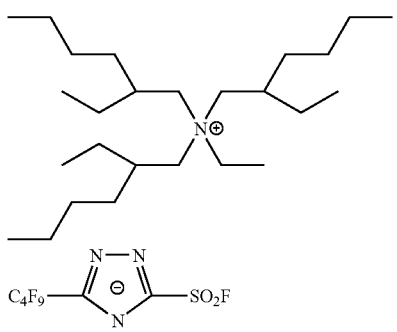

This compound is an antistatic agent, including for nonpolar solvents. At a concentration of 5 mmol in hexane, it induces a conductivity of greater than $10^{-3}$ μS/cm.

EXAMPLE 47

Electrochromic Window

A mixture containing N-(2-acryloylethyl)-N,N,N-trimethylammonium.BFST (40% by weight), LiBFST (17% by weight), poly(ethylene glycol) dimethacrylate having a molar mass of 600 g/mol (42% by weight, Aldrich) and silica particles having a specific surface area of 300 m²/g (1% by weight, Aérosil, Degussa A G) and xanthone was prepared in acetonitrile.

This mixture was spread onto a glass plate covered with a coat of tungsten trioxide $WO_3$ and with a conductive base coat of tin oxide, so as to give a film with a thickness of 25 μm after drying under vacuum at 80° C. A membrane which is optically transparent in the visible range and adherent to the support was thus obtained by photopolymerization triggered by irradiation with a UV lamp for 10 min at 35° C.

An electrochromic system was subsequently prepared by assembling, in a glovebox, a counterelectrode made up by depositing a coat of hydrogenated iridium oxide $H_xIrO_2$ and a base coat of tin oxide onto a glass plate. This electrochrome gave a variation in optical absorption of 80% (bleached state) to 30% (colored state) and good performance levels in terms of cycling. It was thus possible to perform a number of coloring/bleaching cycles of greater than 20 000.

EXAMPLE 48

Corrosion

Button cells were assembled using a sheet of lithium as anode, an aluminum strap as cathode and electrolytes of LiBFST, LiTFST and LiTFSI, prepared according to the process of example 40, in □-butyrolactone. These cells were tested by applying a potential increment of 100 mV at regular intervals between 2 and 5 V, and recording the resulting current. The change in the current as a function of time and for the various potentials makes it possible to compare the phenomenon of aluminum corrosion for LiTFST, LiBFST and LiTFSI. Surprisingly, a much lower corrosion current was observed for LiTFST and LiBFST relative to LiTFSI, despite similar ion conductivities.

EXAMPLE 49

Li—$FeS_2$ and Li—$MnO_2$ Primary Battery

The lithium salt of 3,5-difluorosulfonyl-1,2,4-triazole, LiBFST, as prepared according to example 16, was tested in a primary lithium generator. The battery was produced by superimposing the following layers:
- a stainless steel current collector having a thickness of 2 mm;
- a cathode composed of a deposit, on an aluminum strap, of composite material having a thickness of 100 μm and comprising battery-quality $FeS_2$ (92% by weight, READE), acetylene black (1.4% by weight, Soltex), graphite EBN1010 (4% by weight, Superior Graphite), a poly(vinylidene fluoride) binder (2% by weight, Kureha), micronized polytetrafluoroethylene (0.3% by weight) and fumed silica (0.3% by weight, Degussa);
- an electrolyte comprising a disc of a porous film of Celgard 2500 impregnated with a 0.8 M solution of LiBFST in 1,3-dioxolane/1,2-dimethoxyethane (65%/35% by volume);
- an anode comprising a sheet of lithium metal having a thickness of 50 μm;
- a stainless steel current collector.

The discs constituting the electrodes and the electrolyte were cut up in a glovebox and stacked in the order indicated above, and then impregnated with the electrolyte. The collectors were subsequently placed on either side of the stack obtained.

The whole was sealed in a button cell case, which makes it possible both to protect the generator from the atmosphere and to exert a mechanical stress on the films. The battery was subsequently discharged to 1 V at a discharge rate of C/10 (nominal capacity charged or discharged in 10 hours). 97% of the theoretical capacity of the cathode was thus recovered. Similar assembled generators showed good aging properties, confirming the advantage of the products of the invention for this application. Similar generators were also prepared by replacing LiBFST with lithium triflate; much improved performance levels were noted, in particular during power demand, and more particularly at low temperature (<0° C.).

Similar generators were also assembled by replacing $FeS_2$ with $MnO_2$ of battery quality. These tests confirmed the advantage of the materials of the invention for primary lithium generators, and the improvement in performance levels in terms of power and at low temperature obtained using LiBFST in place of lithium triflate.

EXAMPLE 50

Li/PEO/$V_2O_5$ Battery

The lithium salt of 3,5-difluorosulfonyl-1,2,4-triazole (LiBFST) prepared according to example 8 was tested in an electrochemical generator according to the lithium-polymer technology. The generator was prepared by superimposing the following layers:
  a stainless steel current collector having a thickness of 2 mm;
  a cathode comprising a disc of a film of composite material having a thickness of 100 µm and comprising vanadium dioxide (45% by volume), Shawinigan black (5% by volume) and a polyethylene oxide of mass Mw=3·10$^5$ (50% by volume);
  an electrolyte comprising a disc of a film, having a thickness of 30 µm, of polyethylene oxide of mass Mw=5·10$^6$ containing the LiBFST salt at an O/Li concentration=15/1;
  an anode comprising a sheet of lithium metal having a thickness of 50 µm;
  a current collector similar to the abovementioned collector.

The discs constituting the electrodes and the electrolyte were cut up in a glovebox and stacked in the order indicated above. The collectors were subsequently placed on either side of the stack obtained.

The whole was sealed in a button cell case, which makes it possible both to protect the generator from the atmosphere and to exert a mechanical stress on the films. The battery was then placed in a chamber under argon, placed in an oven at a temperature of 60° C. It was subsequently cycled between 1.8 and 3.3 V at a charge and discharge rate of C/10 (nominal capacity charged or discharged in 10 hours).

A similar result was obtained by replacing LiBFST with the lithium salt of 3-trifluoromethyl-5-fluorosulfonyl-1,2,4-triazole prepared according to example 7, with the lithium salt of 3,5-di(1,1,1-trifluoro-2-ethanoxysulfonyl)-1,2,4-triazole prepared from its potassium salt obtained in example 9 according to the process of example 7, and with the dilithium salt of $FSO_2$-TrLi—($CF_2$)-2-TrLi—$SO_2F$ prepared by exchange between the corresponding potassium salt and LiCl in THF. In the latter case, an improvement in the performance levels was noted during power demand, probably linked to the dianionic nature of the salt increasing the lithium transport number.

EXAMPLE 51

Battery

The $PYR_{13}$BFST Compound

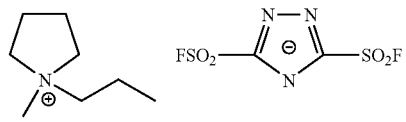

prepared according to example 27 was tested in an electrochemical generator of lithium-gel polymer technology.

The generator was prepared by superimposing the following layers:
  a stainless steel current collector having a thickness of 2 mm;
  a cathode comprising a disc of a film, deposited onto a steel strap, of composite material having a thickness of 80 µm and comprising carbon-coated LiFePO$_4$ (43% by weight, Phostec Lithium Inc.), Shawinigan black (7% by weight), a polyethylene oxide (PEO) of mass Mw=4·10$^6$ (18% by weight), the lithium salt LiBFST (7% by weight) and $PYR_{13}$BFST (25% by weight);
  an electrolyte having a thickness of 30 µm and comprising a disc of a film of polyethylene oxide PEO of mass Mw=4·10$^6$ containing a mixture of LiBFST and of $PYR_{13}$BFST, the LiBFST concentration being such that O/Li=15/1 for Li provided by LiBFST, the $PYR_{13}$BFST/ P(EO)$_{15}$LiBFST molar ratio being 2:1;
  an anode comprising a sheet of metal lithium having a thickness of 50 µm;
  a stainless steel current collector having a thickness of 2 mm.

The discs constituting the electrodes and the electrolyte were cut up in a glovebox and stacked in the order indicated above. The collectors were subsequently placed on either side of the stack obtained.

The whole was sealed in a button cell case, which makes it possible both to protect the generator from the atmosphere and to exert a mechanical stress on the films, and then the battery was brought to 80° C. for 30 minutes in order to ensure a good interface between the layers. The battery was then placed in a chamber under argon, placed in an oven at a temperature of 40° C. It was subsequently cycled between 2.5 and 3.6 V at a charge and discharge rate of C/10 (nominal capacity charged or discharged in 10 hours). The first charge made it possible to determine that the specific capacity of the cathode is 157 mAh/g. This capacity was more than 90% maintained after 100 cycles. Another generator produced under the same conditions, but replacing the compound of example 27 with the DEMMOA.BFST compound of example 17, gave similar results.

EXAMPLE 52

Li/Liquid Electrolyte/Natural Graphite Battery

The lithium salt of 3,5-difluorosulfonyl-1,2,4-triazole, LiBFST, as prepared according to example 8, was tested in an electrochemical generator according to lithium-ion technology using a carbon-coated $LiFePO_4$ cathode.

A generator which has a lithium anode and a graphite cathode was assembled in order to evaluate the performance levels of this salt with respect to graphite. The generator was produced by superimposing the following layers:

- a stainless steel current collector having a thickness of 2 mm;
- a cathode comprising a disc of a film, deposited on a copper strap, of composite material having a thickness of 80 μm and comprising natural graphite GN SL20 (90% by weight, Superior Graphite), and a polyvinylidene fluoride binder (10% by weight, Kureha);
- an electrolyte comprising a disc of a porous film of Celgard 2500 impregnated with a 1M solution of LiBFST in ethylene carbonate/diethyl carbonate, EC/DEC (1/1 by weight);
- an anode comprising a sheet of metal lithium having a thickness of 50 μm;
- a stainless steel current collector.

The discs constituting the electrodes and the electrolyte were cut up in a glovebox and stacked in the order indicated above, and then impregnated with the electrolyte. The collectors were subsequently placed on either side of the stack obtained.

The whole was sealed in a button cell case, which makes it possible both to protect the generator from the atmosphere and to exert a mechanical stress on the films. The battery subsequently performed two cycles between 1 V and 0.01 V at a charge and discharge rate of C/25 (nominal capacity charged or discharged in 10 hours).

This battery has an impedance equivalent to a battery using a reference electrolyte of 1M $LiPF_6$ in EC/DEC (1/1). The reversible capacity is 363 mAh/g, confirming the compatibility of LiBFST with the graphite anode of a Li-Ion technology battery, in particular with respect to the formation of the passivation layer on the graphite, which is a key element.

An identical generator was produced by replacing the LiBFST salt of example 8 with the LiTFST salt of example 7. Poor passivation of the graphite electrode was noted. Even if the difficulties associated with the formation of the passivation layer can be resolved by using additives such as vinylidene carbonate, this result shows the particular advantage of LiBFST for a Li-Ion technology battery using a carbon anode.

A generator was subsequently constructed by superimposing:

- a stainless steel current collector having a thickness of 2 mm;
- an anode comprising a disc of a film, deposited on a copper strap, of composite material having a thickness of 110 μm and comprising natural graphite SL20 (90% by weight, Superior Graphite) and a polyvinylidene fluoride binder (10% by weight, Kureha);
- an electrolyte comprising a disc of a porous film of Celgard 2500 impregnated with a 1M solution of LiBFST in EC/DEC (1/1 by weight) containing, in addition, 3% by weight of vinylidene carbonate (VC), which is known to improve the performance levels of the passivation level of the anode;
- a cathode comprising a disc of a film, deposited on an aluminum strap, of composite material having a thickness of 110 μm and comprising $C-LiFePO_4$ (90% by weight, Phostech Lithium), and a polyvinylidene fluoride binder (10% by weight, Kureha);
- a stainless steel current collector.

The whole was sealed in a button cell case. The battery subsequently performed two cycles between 2.5 V and 3.7 V by slow cyclic voltametry (20 mV/s). It was thus possible to determine a specific capacity of 154 mAh/g for $C-LiFePO_4$. The battery was subsequently cycled at a charge and discharge rate of C/10. This capacity was more than 90% maintained after 300 cycles.

A similar battery was also tested by performing the cycling at a rate of C/4 at a temperature of 60° C. The loss of capacity over 100 cycles was less than 2%.

A similar battery was also tested, by replacing the EC/DEC electrolyte solvent with the N-methyl-N-methoxymethylpyrrolidinium BFST containing 3% by weight of vinylidene carbonate. At 25° C. and a charge/discharge rate of C/10, the initial specific capacity (151 mAh/g) was more than 90% maintained after 50 cycles. A generator using N,N-diethyl-N-methyl-N-(2-methoxyethyl)ammonium BFST instead of the pyrrolidinium gave similar results.

A similar battery was also tested, replacing the 1M LiBFST EC/DEC electrolyte with 1-ethyl-3-methylimidazolium BFST containing 1M LiTFSI. At 25° C. and a charge/discharge rate of C/10, the initial specific capacity (153 mAh/g) was more than 90% maintained after 20 cycles.

A similar battery, with a gel electrolyte formed in-situ by adding, to the composition of the 1 M LiBFST EC/DEC+3% VC electrolyte, 5% by weight of a 1:1 (molar) mixture of poly(ethylene glycol) dimethacrylate having a molar mass of 600 g/mol (Aldrich) and of tri(ethylene glycol) divinyl ether, this mixture containing 1% by weight of 2,2'-azobis[2-(2-imidazolinium-2-yl)propane] BFST prepared in example 13, was also tested. This cell was subsequently brought to 1 hour at 80° C., and a battery with a gel electrolyte prepared in-suit was thus obtained. After cycling at 60° C. at a rate of C/2, this battery exhibits a capacity loss of less than 3% after 100 cycles.

EXAMPLE 53

Natural Graphite/Liquid Electrolyte/$LiMn_2O_4$ Battery

A Li-ion generator similar to that of example 52 was assembled by replacing $C-LiFePO_4$ with battery-quality $LiMn_2O_4$ (LiCo Technology Corp.) deposited onto a carbon-coated aluminum strap (Intellicoat). An NG/1M LiBFST EC:DEC (1/1 by weight)+3% VC/$LiMn_2O_4$ generator (Gen-A) was thus obtained.

A generator was assembled in the same manner, using $LiPF_6$ instead of LiBFST (Gen-B).

In the two cases, 250 ppm of water were added to the electrolyte before assembly. These two batteries were cycled at a rate of C/4 (a specific capacity of 103 mAh/g was determined beforehand by slow voltametry) between 2.5 V and 3.9 V, at a temperature of 55° C. After 50 cycles, Gen-A still exhibited 70% of the capacity at the first cycle; on the other hand, Gen-B exhibited only 30% of the capacity at the first cycle, illustrating the better resistance to hydrolysis of LiBFST with respect to $LiPF_6$.

EXAMPLE 54

Carbon/Liquid Electrolyte/$LiCoO_2$ Battery

A Li-ion generator similar to that of example 52 was assembled, in a Swagelok assembly, by replacing $C-LiFePO_4$ with battery-quality $LiCoO_2$ (LiCo Technology Corp.), and the solvent with □-butyrolactone (GBL) containing 3% of VC. An NG/1M LiBFST GBL+3% VCILiCoO$_2$ generator (Gen-A) was thus obtained.

A generator was assembled in the same manner, using LiPF$_6$ instead of LiBFST (Gen-B).

The batteries subsequently performed two cycles between 2.5 V and 4.2 V at a charge and discharge rate of C/25, the battery ending in the charged state. The two electrodes were then isolated in a glovebox and the anode was placed in a DSC apparatus with set heating of 10° C./min. An exothermic peak was observed with LiPF$_6$ at around 140° C. On the other hand, the peak with LiBFST is shifted to around 170° C., i.e. a gain of 30° C.

Similar batteries were assembled using, as electrolyte, EC/EMC (3/7 by weight) containing a 1 M mixture of LiBFST/LiPF$_6$ (1/9 molar)+3% VC (Gen-C), and EC/EMC (3/7 by weight) containing 1M LiPF$_6$+3% VC (Gen-D). The batteries subsequently performed two cycles between 4.2 V and 2.5 V at a charge and discharge rate of C/25. A 30% reduction in gas generation during the formation of the passivation layer on the anode was observed with the battery using the LiBFST/LiPF$_6$ mixture.

Similar batteries were assembled using C—LiFePO$_4$ as cathode and, as electrolyte, EC/EMC (3/7 by weight) containing a 1 M mixture of LiBFST/LiPF$_6$ (9/1 molar)+3% VC (Gen-C), and EC/EMC (3/7 by weight) containing a 1 M mixture of LiBFST/LiBF$_4$/LiPF$_6$ (8/1/1 molar)+3% VC (Gen-D), as was a battery using only LiBFST (Gen-E). The batteries were subsequently cycled between 4.1 V and 2.5 V at a charge and discharge rate of C/2, this being at a temperature of 60° C. The loss of capacity over 200 cycles was less than 3% of the capacity for Gen-D, 5% for Gen-C and 8% for Gen-E. The improvement is probably linked to a protective effect on the aluminum collector.

These results show the advantage of the formulations of electrolytes containing the LiPF$_6$ and/or LiBF$_4$ anions, ranging from predominantly LiPF$_6$ and/or LiBF$_4$ fractions to predominantly LiBFST fractions.

The invention claimed is:

1. An ionic compound comprising at least one anionic part associated with at least one cationic part M in a number which grants electronic neutrality to the compound, wherein M is H$^+$, or a cation of valence m wherein $1 \leq m \leq 4$, and wherein the anionic part has formula

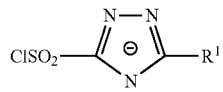

(I)

wherein R$^1$ represents:
a ClSO$_2$— group;
a group R$_F$ selected from the group consisting of HCF$_2$—, HCF$_2$CF$_2$—, and linear or branched perfluoroalkyl groups having 1 to 12 carbon atoms wherein the chain may optionally be interrupted by at least one divalent oxygen atom linked to two carbon atoms; or
a group of formula

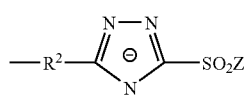

(Ia)

wherein Z is Cl and R$^2$ is a linear or branched perfluoroalkylene group having 2 to 12 carbon atoms wherein the chain may optionally be interrupted by at least one divalent oxygen atom linked to two carbon atoms.

2. A compound according to claim 1, said compound having one of the fomulae ClSO$_2$-TrM-SO$_2$Cl, ClSO$_2$-TrM-CF$_3$ or ClSO$_2$-TrM-R$^2$-TrM-SO$_2$Cl, wherein TrM represents an anionic 1,2,4-triazole group associated to the cation M.

3. A compound according to claim 1, wherein R$_F$ is selected from the group consisting of HCF$_2$—, HCF$_2$—CF$_2$—, C$_2$F$_5$—, C$_4$F$_9$—, CF$_3$—CF$_2$—CF$_2$—O—CF(CF$_3$)— and CF$_3$—CF$_2$—CF$_2$—O—CF(CF$_3$)—CF$_2$—CF(CF$_3$)—.

4. A compound according to claim 1, wherein M is selected from the group consisting of hydroxonium, oxonium, nitrosonium, ammonium cations, metal cations of valence m, organic cations of valence m, and organometallic cations of valence m, wherein m is $1 \leq m \leq 4$.

5. A compound according to claim 4, wherein M is selected from the group consisting of H$^+$, NH$_4^+$ and alkali metal cations.

6. A fluorosulfonyl compound comprising at least one anionic part associated with at least one cationic part M' in a number which grants electronic neutrality to the compound, wherein M' is H$^+$, or a cation of valence m wherein $1 \leq m \leq 4$, and wherein the anionic part has formula

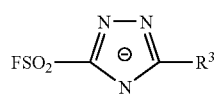

(II)

wherein R$^3$ represents:
a FSO$_2$— group;
a group R$_F$ selected from the group consisting of HCF$_2$—, HCF$_2$CF$_2$—, and linear or branched perfluoroalkyl groups having 1 to 12 carbon atoms wherein the chain may optionally be interrupted by at least one divalent oxygen atom linked to two carbon atoms; or
a group of formula

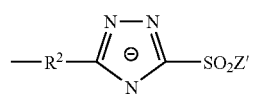

(IIa)

wherein Z' is F and R$^2$ is a linear or branched perfluoroalkylene group having 2 to 12 carbon atoms wherein the chain may optionally be interrupted by at least one divalent oxygen atom linked to two carbon atoms.

7. The compound of claim 6, said compound having one of the formulae FSO$_2$-TrM'-SO$_2$F, FSO$_2$-TrM'-CF$_3$ or FSO$_2$-TrM'-R$^2$-TrM'-SO$_2$F, wherein TrM' represents an anionic 1,2,4-triazole group associated to the cation M'.

8. The compound of claim 6, wherein M' is a metal cation selected from the group consisting of alkali metal cations, alkali earth metal cations, transition metal cations, trivalent metal cations and rare earth metal cations.

9. The compound of claim 6, wherein M' is an organometallic cation selected from the group consisting of ferrocene cations; ruthenocene cations; titanocene cations; zirconocene cations; indenocenium cations; arene metallocenium cations; cations of transition metal complexed by phosphine ligands; and cations having one or more alkyl or aryl groups covalently linked to a metal atom or to a group of metal atoms.

10. The compound of claim 6, wherein M' is a nitrosonium cation.

11. The compound of claim 6, wherein M' is an onium cation, selected from the group consisting of hydroxonium, oxonium, ammonium, amidinium, guanidinium, pyridinium, quinolinium, imidazolium, pyrazolium, imidazolinium, triazolium, sulfonium, phosphonium, pholium, phosphorolium, iodonium, carbonium, pyridazinium, pyrimidinium, pyrrolidinium, thiazolium, oxazolium, uronium, thiouronium, pyrazinium, piperazinium, piperidinium, pyrrolium, pyrizinium, thiomorpholinium and morpholinium cations.

12. A fluoroalkoxysulfonyl compound comprising at least one anionic part associated with at least one cationic part M" in a number which grants electronic neutrality to the compound, wherein M" is $H^+$, or a cation of valence m wherein $1 \leq m \leq 4$, and wherein the anionic part has formula

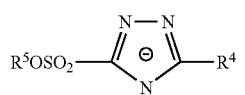 (III)

or $R_F\text{-TrM"-SO}_2\text{—O—R}^9\text{—O—SO}_2\text{-TrM"-}R_F$ (III')

wherein $R^4$ represents:
a group $R^5\text{—O—SO}_2\text{—}$;
a group $R_F$ selected from the group consisting of $HCF_2\text{—}$, $HCF_2CF_2\text{—}$, and linear or branched perfluoroalkyl groups having 1 to 12 carbon atoms wherein the chain may optionally be interrupted by at least one divalent oxygen atom linked to two carbon atoms; or
a group of formula

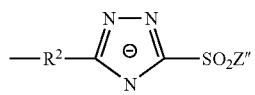 (IIIa)

wherein Z" is selected from the group consisting of F and $R^5\text{—O—}$, and $R^2$ is a linear or branched perfluoroalkyl group having 2 to 12 carbon atoms wherein the chain may be interrupted by at least one divalent oxygen atom linked to two carbon atoms;

wherein $R^5$ represents a $R^6CH_2\text{—}$ group, a $R^6R^7CH\text{—}$ group or a $R^6R^7R^8CH\text{—}$ group wherein groups $R^6$, $R^7$ and $R^8$ represent a perfluorinated linear or branched alkyl group having 1 to 12 carbon atoms, the chain of which is optionally interrupted by at least one divalent oxygen atom linked to two carbon atoms;

wherein $R^9$ represents a perfluorinated linear or branched alkylene group having 2 to 12 carbon atoms, the chain of which is optionally interrupted by at least one divalent oxygen atom linked to two carbon atoms; and wherein TrM" represents an anionic 1,2,4-triazole group associated to cation M".

13. A compound according to claim 12, which has one of the formulae $R^5\text{—O—SO}_2\text{-TrM"-SO}_2\text{—O—R}^5$, $R^5\text{—O—SO}_2\text{-TrM"-}R^2\text{-TrM"-SO}_2\text{—O—R}^5$ and $R^5\text{—O—SO}_2\text{-TrM"-}CF_3$.

14. The compound of claim 12, wherein M" is a metal cation selected from the group consisting of alkali metal cations, alkali earth metal cations, transition metal cations, trivalent metal cations and rare earth metal cations.

15. The compound of claim 12, wherein M" is an organometallic cation selected from the group consisting of ferrocene cations; ruthenocene cations; titanocene cations; zirconocene cations; indenocenium cations; arene metallocenium cations; cations of transition metal complexed phosphine ligands; and cations having one or more alkyl or aryl groups covalently linked to a metal atom or to a group of metal atoms.

16. The compound of claim 12, wherein M" is a nitrosonium cation.

17. The compound of claim 12, wherein M" is an onium cation, selected from the group consisting of hydroxonium, oxonium, ammonium, amidinium, guanidinium, pyridinium, quinolinium, imidazolium, pyrazolium, imidazolinium, triazolium, sulfonium, phosphonium, pholium, phosphorolium, iodonium, carbonium, pyridazinium, pyrimidinium, pyrrolidinium, thiazolium, oxazolium, uronium, thiouronium, pyrazinium, piperazinium, piperidinium, pyrrolium, pyrizinium, thiomorpholinium and morpholinium cations.

18. Polymer IV consisting of repeat units having a formula $[\text{—O}_2\text{S-TrM*-SO}_{2OCH_2}\text{—R}^9\text{—CH}_2\text{O—}]$ or $[\text{—O}_2\text{S-TrM*-R}^2\text{-TrM*-SO}_2\text{OCH}_2\text{—R}^9\text{—CH}_2\text{O—}]$ wherein:
$R^2$ is a linear or branched perfluoroalkylene group having 2 to 12 carbon atoms wherein the chain may be interrupted by at least one divalent oxygen atom linked to two carbon atoms;
M* is $H^+$, or a cation of valence m wherein $1 \leq m \leq 4$,
TrM* represents an anionic triazole-1,2,4 group associated to cation M*;
$R^9$ is a linear or branched perfluoroalkylene group having 2 to 12 carbon atoms wherein the chain may be optionally interrupted by at least one divalent oxygen atom.

19. The polymer IV of claim 18, wherein M* is a metal cation selected from alkali metal cations, alkali earth metal cations, transition metal cations, trivalent metal cations or rare earth metal cations.

20. The polymer IV of claim 18, wherein M* is an organometallic cation selected from the group consisting of ferrocene cations; ruthenocene cations; titanocene cations]; zirconocene cations; indenocenium cations; arene metallocenium cations; cations of transition metal complexed phosphine ligands; and cations having one or more alkyl or aryl groups covalently linked to a metal atom or to a group of metal atoms.

21. The polymer IV of claim 18, wherein M* is a nitrosonium cation.

22. The polymer IV of claim 18, wherein M* is an onium cation, selected from the group consisting of hydroxonium, oxonium, ammonium, amidinium, guanidinium, pyridinium, quinolinium, imidazolium, pyrazolium, imidazolinium, triazolium, sulfonium, phosphonium, pholium, phosphorolium, iodonium, carbonium, pyridazinium, pyrimidinium, pyrrolidinium, thiazolium, oxazolium, uronium, thiouronium, pyrazinium, piperazinium, piperidinium, pyrrolium, pyrizinium, thiomorpholinium and morpholinium cations.

\* \* \* \* \*